(12) United States Patent
Fliri et al.

(10) Patent No.: US 6,521,630 B1
(45) Date of Patent: Feb. 18, 2003

(54) TETRAHYDROQUINAZOLINE-2,4-DIONES AND THERAPEUTIC USES THEREOF

(75) Inventors: Anton Franz Joseph Fliri, Stonington, CT (US); Todd William Butler, Salem, CT (US); Randall James Gallaschun, Lebanon, CT (US); John Anthony Ragan, Gales Ferry, CT (US); Brian Patrick Jones, Coventry, RI (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/650,486

(22) Filed: Aug. 29, 2000

Related U.S. Application Data

(60) Provisional application No. 60/151,725, filed on Aug. 31, 1999.

(51) Int. Cl.[7] .................. A61K 31/517; C07D 419/00
(52) U.S. Cl. .................. 514/266.2; 544/284; 544/285
(58) Field of Search .................. 514/266.2; 544/284, 544/285

(56) References Cited

U.S. PATENT DOCUMENTS

| | | | |
|---|---|---|---|
| 3,274,194 A | 9/1966 | Hayao | 260/256.4 |
| 3,726,979 A | 4/1973 | Hong | 424/251 |
| 3,879,393 A | 4/1975 | Havera | 260/256.4 |
| 3,919,425 A | 11/1975 | Vidrio | 424/251 |
| 4,684,654 A | 8/1987 | Wright, Jr. et al. | 514/259 |
| 5,264,438 A | 11/1993 | Shimazaki et al. | 514/259 |
| 5,296,487 A | 3/1994 | Shimazaki et al. | 514/259 |

FOREIGN PATENT DOCUMENTS

| | | |
|---|---|---|
| EP | 0184258 | 6/1986 |
| EP | 0436157 | 7/1991 |
| EP | 0481342 | 4/1992 |
| EP | 0350403 | 1/1993 |
| EP | 1083178 | 3/2001 |
| JP | 64-6269 | 1/1989 |
| WO | WO9305035 | 3/1993 |
| WO | WO9747601 | 12/1997 |

OTHER PUBLICATIONS

E. P. Papadopoulos, "Reactions of Derivatives of Anthranilic Acid With 3–Chloropropyl Isocyanate", *J. Heterocylic Chem.*, 21 1411 (1984).

Villalobos–Molina et al., "The 5–HT$_2$ Receptor Antagonist, Pelanserin, Inhibits α$_1$–Adrenoceptor–Mediated Vasoconstriction in Vitro", *Eur. J. Pharmacol.* (1995), 277(2/3), 181–5.

Villalobos–Molina et al., "Pelanserin Inhibition of Serotonin–Induced Phosphatidylinositol Turnover and Contraction in Rabbit Aorta", *Drug. Dev. Res.* (1991), 23(3), 281–7.

Hong et al., "Mechanism of the Antihypertensive Effect of TR2515, A Potent Serotonin Antagonist", *Proc. West. Pharmacol. Soc.* (1984), 27, 1–4.

*Primary Examiner*—Mukund J. Shah
*Assistant Examiner*—Tamthom N. Truong
(74) *Attorney, Agent, or Firm*—P. C. Richardson; P. H. Ginsburg; A. D. Joran

(57) ABSTRACT

The present invention relates to tetrahydroquinazoline-2,4-diones derivatives of the formula (I):

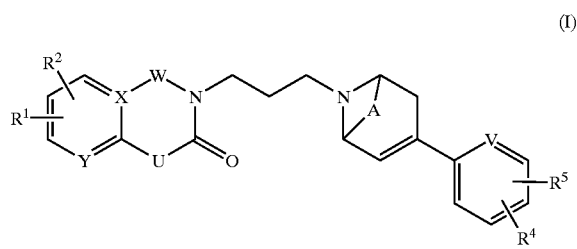

pharmaceutically acceptable salts thereof, wherein A is $(CH_2)_n$ where n is equal to 0, 1 or 2; U is $CH_2$, NH, or $NR^3$, $R^1$ and $R^2$ are selected independently from H, $(C_1-C_6)$alkyl, Cl, F, CN, nitro, $CF_3$, —$NHC(O)R^6$ and —$OR^7$, or $R^1$ and $R^2$, together with the atoms to which they are attached, form a carbocyclic or heterocyclic five- or six-membered ring, $R^3$ is selected from the group consisting of H, $(C_1-C_6)_m$alkyl, $C(=O)$—$(C_1-C_6)$alkyl, where m=1 or 2; $R^4$ and $R^5$ are selected from H, $(C_1-C_6)$alkyl, Cl, F, —$CF_3$, —CN, —NHC$(=O)R^6$, —$OR^7$, a 5-to 7-membered aryl or heteroaryl ring, where m, $R^6$ and $R^7$ are as defined above; and $R^6$ and $R^7$ are selected independently from H, $(C_1-C_6)$alkyl or a 5- to 7-membered aryl or heteroaryl ring; V is CH, $CR^3$, or N; W is $CH_2$, C(O), or $S(O)_2$; X is C or N; and Y is CH, $CR^1,CR^2$, or N. The invention also relates to pharmaceutical compositions containing the same and to methods of use thereof, including in the inhibition of serotonin reuptake, the inhibition of the binding of 5-HT$_{2A}$ serotonin receptors and the treatment of diseases, conditions or disorders of the central nervous system. Further, the present invention is also directed to methods for the preparation of 4-(4-phenyl-1,2,3,6-tetrahydropyridin-1-yl)-propyl-1,2,3,4-tetrahydroquinazoline-2,4-dione compounds and intermediates useful thereof.

14 Claims, No Drawings

TETRAHYDROQUINAZOLINE-2,4-DIONES AND THERAPEUTIC USES THEREOF

The application claims the benefit of U.S. provisional patent application No. 60/151,725, filed Aug. 31, 1999.

BACKGROUND OF THE INVENTION

The present invention is directed to 4-(4-phenyl-1,2,3,6-tetrahydropyridin-1yl)-propyl-1,2,3,4-tetrahydroquinazoline-2,4-dione compounds, and pharmaceutically acceptable salts thereof, as well as to the use of these compounds to selectively block serotonin reuptake and 5-HT$_{2A}$ receptor binding in mammalian central nervous systems (CNS). The present invention is also directed to the use of these compounds in a methods of treatment of various diseases, disorders and conditions, as well as pharmaceutical compositions useful therefor. Further, the present invention is directed to methods for the preparation of 4-(4-phenyl-1,2,3,6-tetrahydropyridin-1-yl)propyl-1,2,3,4-tetrahydroquinazoline-2,4-dione compounds and intermediates useful therefore.

Serotonin (5-hydroxytryptamine, "5-HT") is a monoamine neurotransmitter active in the central nervous systems ("CNS") of mammals, including humans. The cell bodies of serotoninergic cells are located in the brain stem, and the axons project therefrom into a variety of other areas, e.g., the amygdala, hippocampus, hypothalamus, nucleus accumbens and the striatum. Serotonin-producing cells store the neurotransmitter in intracellular vesicles, where it is either converted with monoamine oxidase ("MAO," EC 1.4.3.4) into 5-hydroxyindoleacetic acid ("5-HIAA") or released into synapses. In the synapses, serotonin is either resorbed into the presynaptic neurons and stored within intracellular vesicles of the presynaptic neurons or remains available for interaction with serotonin receptors, e.g., the 5-HT$_{2A}$ receptor, in post-synaptic membranes.

Altered functioning of this serotonin-based neurotransmission system has been implicated (see, e.g., Lancet, 2:717–719 (1989)) in a variety of CNS-related disorders, both psychiatric and non-psychiatric. These disorders include, without limitation, schizophrenia, psychosis, depression, aggression, sleep disorders, anxiety disorders, migraines, compulsive disorders, bipolar disorders, vision disorders, emesis, feeding disorders, learning disorders, sexual behavior disorders, phobias and substance abuse disorders. Compounds that either block serotonin reuptake into presynaptic neurons or that antagonize its interaction with post-synaptic membrane receptors have a wide variety of potential applications in the treatment of mammals, including humans, afflicted with CNS-related disorders. The compounds act to restore some semblance of normal neurotransmitter functioning. Moreover, compounds which accomplish these objectives selectively can be used with a lower risk of attendant and unwanted side effects, e.g., sexual dysfunction et al.

Shimazaki et al (U.S. Pat. No. 5,296,487) describe quinazoline derivatives having activity as serotonergic, as well as alpha-adrenergic and dopaminergic, agents. However, the compounds disclosed in that reference are not known to avoid common side effects such as sexual dysfunction. In addition, while Shimazaki et al. describe the serotonergic activity of such compounds as being due to serotonin receptor antagonism, Shimazaki et al. do not describe the serotonergic activity of these compounds as that of a serotonin reuptake inhibitor and effective for the treatment of schizophrenia, psychosis, depression, aggression, sleep disorders, anxiety disorders, migraines, compulsive disorders, bipolar disorders, vision disorders, emesis, feeding disorders, learning disorders, sexual behavior disorders, phobias and substance abuse. Moreover, the examples described by Shimazaki et al. are limited to compounds that have a butyl linker between the quinazolinedione and the tetrahydropyridyl moiety. In contrast, this invention discloses compounds with a propyl link between the quinazolinedione and the tetrahydropyridine moiety which is a critical element in these compounds for substantially increasing receptor selectivity and for decreasing cardiovascular and peripheral side effects necessary for treating central nervous system disorders as disclosed in this invention.

Wade et al. (U.S. Pat. No. 4,007,191) describe tetrahydropyridyl-alkyl 2,3-dihydro-3-hydroxy-1H-benz(de)isoquinolin-1-ones having antidepressant activity. Hong et al. (U.S. Pat. No. 3,726,979) describe serotonin-antagonist quinazoline derivatives. Vidrio et al. (U.S. Pat. No. 3,919,425) indicate that certain 3 substituted 2,4-dioxoquinazolines have vasodilating activity. Shin et al. (U.S. Pat. No. 3,274,194) describe quinazoline dione derivatives that have anti-inflammatory and sedating activity. Moreover, Villalobos-Molina et al. (Eur. J. Pharmacol., 277(2/3):181–5 (1995) and Drug Dev. Res. 23(3): 281–7 (1991)) describe 2,4-(1H,3H)-quiazolinedione-3-[3-(4-phenyl-1-piperazinyl)propyl] (pelanserine) as having blood pressure lowering, 5-HT$_{2A}$ serotonin receptor binding activity. However, none of these documents describe or suggest either the 4-(4-phenyl-1,2,3,6-tetrahydropyridin-1-yl)-propyl-1,2,3,4-tetrahydroquinazoline-2,4-dione compounds of the present invention, provided herein, or the therapeutic uses of the present invention.

SUMMARY OF THE INVENTION

The present invention provides 4-(4-phenyl-1,2,3,6-tetrahydropyridin-1-yl)-propyl-1,2,3,4-tetrahydroquinazoline-2,4-dione compounds of formula (I):

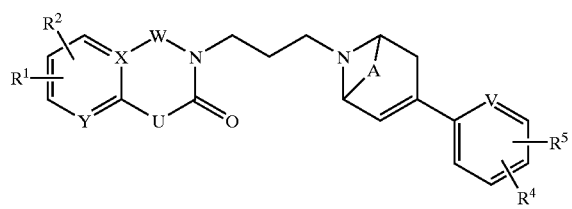

(I)

and pharmaceutically acceptable salts thereof, wherein

A is (CH$_2$)$_n$ where n is equal to 0, 1 or 2;

U is CH$_2$, NH, or NR$^3$,
where R$^3$ is selected from the group consisting of H, (C$_1$–C$_6$)$_m$alkyl, C(=O)—(C$_1$–C$_6$)alkyl, where m=1 or 2;

R$^1$ and R$^2$ are selected independently from H, (C$_1$–C$_6$) alkyl, Cl, F, CN, nitro, CF$_3$, —NHC(O)R$^6$ and —OR$^7$, or R$^1$ and R$^2$, together with the atoms to which they are attached, form a carbocyclic or heterocyclic five- or six-membered ring,
where R$^6$ and R$^7$ are selected independently from H, (C$_1$–C$_6$)alkyl or a 5- to 7 membered aryl or heteroaryl ring;

R$^4$ and R$^5$ are selected from H, (C$_1$–C$_6$)alkyl, Cl, F, —CF$_3$, —CN, —NHC(=O)R$^6$, —OR$^7$, a 5-to 7-membered aryl or heteroaryl ring, where m, $R^6$ and $R^7$ are as defined above;

V is CH, $CR^3$, or N, where $R^3$ is as defined above;

W is $CH_2$, C(O), or $S(O)_2$;

X is C or N;

Y is CH, $CR^1$, $CR^2$, or N, where $R^1$ and $R^2$ are as defined above.

The present invention also relates to methods for preparing compounds of formula (I). In addition, the present invention provides a method for inhibiting serotonin reuptake or serotonin receptor binding in the central nervous system of a mammal, said method comprising administering to the mammal a serotonin receptor binding-inhibiting effective amount or a serotonin reuptake-inhibiting effective amount of a compound of formula (I) or a pharmaceutically acceptable salt thereof. This invention further provides a method of treating a mammal afflicted with various diseases, disorders and conditions, said method comprising administering to the mammal a therapeutically effective amount of a compound of formula I.

Preferred compounds of formula (I) are those wherein A is $(CH_2)_n$ where n is equal to 1 or 2, and U, V, W, X, Y, $R^1$, $R^2$, $R^3$, $R^4$, $R^5$, $R^6$ and $R^7$ are as defined above.

Other preferred compounds of formula (I) are those wherein n is equal to zero (i.e. without a bridging A group); W is C(=O); X is C; Y is C; V is CH or N; and U, $R^1$, $R^2$, $R^3$, $R^4$, $R^5$, $R^6$ and $R^7$ are as defined above.

More preferred compounds of formula (I) are those wherein n is equal to zero (i.e. without a bridging A group); W is C(=O); X is C; Y is C; V is CH or N; U is NH, and $R^1$, $R^2$, $R^4$, $R^5$ are independently chosen from the group consisting of hydrogen, halo, —$CF_3$, nitro, $(C_1-C_6)$alkyl, hydroxy or methoxy.

In the most preferred embodiments of this invention, n is equal to zero (i.e. without a bridging A group); W is C(=O); X is C; Y is C; V is CH; U is NH, and $R^1$, $R^2$, $R^4$, $R^5$ are independently chosen from the group consisting of hydrogen, halo, —$CF_3$, nitro, methyl, hydroxy or methoxy.

Specifically, the more preferred embodiments of this invention are:

5-Chloro-3-{3-[4-(4-chloro-phenyl)-3,6-dihydro-2H-pyridin-1-yl]-propyl}-1H-quinazoline-2,4-dione;

6-Chloro-3-{3-[4-(4-chloro-phenyl)-3,6-dihydro-2H-pyridin-1-yl]-propyl}-1H-quinazoline-2,4-dione;

7-Chloro-3-{3-[4-(4-chloro-phenyl)-3,6-dihydro-2H-pyridin-1-yl]-propyl}-1H-quinazoline-2,4-dione;

5,8-Dichloro-3-{3-[4-(4-chloro-phenyl)-3,6-dihydro-2H-pyridin-1-yl]-propyl}-1H-quinazoline-2,4-dione;

6,8-Dichloro-3-{3-[4-(4-chloro-phenyl)-3,6-dihydro-2H-pyridin-1-yl]-propyl}-1H-quinazoline-2,4-dione;

3-{3-[4-(4-Chloro-phenyl)-3,6-dihydro-2H-pyridin-1-yl]-propyl}-5-methyl1H-quinazoline-2,4-dione;

3-{3-[4-(4-Chloro-phenyl)-3,6-dihydro-2H-pyridin-1-yl]-propyl}-7-methyl1H-quinazoline-2,4-dione;

3-{3-[4-(4-Chloro-phenyl)-3,6-dihydro-2H-pyridin-1-yl]-propyl}-8-methyl1H-quinazoline-2,4-dione;

3-{3-[4-(4-Chloro-phenyl)-3,6-dihydro-2H-pyridin-1-yl]-propyl}-5,8-dimethyl-1H-quinazoline-2,4-dione;

3-{3-[4-(4-Chloro-phenyl)-3,6-dihydro-2H-pyridin-1-yl]-propyl}-6,8-dimethyl-1H-quinazoline-2,4-dione;

3-{3-[4-(4-Chloro-phenyl)-3,6-dihydro-2H-pyridin-1-yl]-propyl}-8trifluoromethyl-1H-quinazoline-2,4-dione;

3-{3-[4-(4-Chloro-phenyl)-3,6-dihydro-2H-pyridin-1-yl]-propyl}-8-hydroxy-1H-quinazoline-2,4-dione;

7-Chloro-3-{3-[4-(4-chloro-phenyl)-3,6-dihydro-2H-pyridin-1-yl]-propyl}-8-methyl-1H-quinazoline-2,4-dione;

8-Bromo-3-{3-[4-(4-chloro-phenyl)-3,6-dihydro-2H-pyridin-1-yl]-propyl}-6-methyl-1H-quinazoline-2,4-dione;

3-{3-[4-(4-Chloro-phenyl)-3,6-dihydro-2H-pyridin-1-yl]-propyl}-6-nitro-1H-quinazoline-2,4-dione;

3-{3-[4-(4-Chloro-phenyl)-3,6-dihydro-2H-pyridin-1-yl]-propyl}-7-nitro-1H-quinazoline-2,4-dione;

5-Methyl-3-[3-(4-p-tolyl-3,6-dihydro-2H-pyridin-1-yl)-propyl]-1H-quinazoline-2,4-dione;

8-Chloro-3-{3-[4-(3-trifluoromethyl-phenyl)-3,6-dihydro-2H-pyridin-1-yl]-propyl}-1H-quinazoline-2,4-dione;

8-Chloro-3-{3-[4-(3-chloro-phenyl)-3,6-dihydro-2H-pyridin-1-yl]-propyl}-1H-quinazoline-2,4-dione;

5-Methyl-3-{3-[4-(3-trifluoromethyl-phenyl)-3,6-dihydro-2H-pyridin-1-yl]-propyl}1H-quinazoline-2,4-dione;

3-{3-[4-(3-Chloro-phenyl)-3,6-dihydro-2H-pyridin-1-yl]-propyl}-5-methyl1H-quinazoline-2,4-dione;

8-Chloro-3-[3-(4-m-tolyl-3,6-dihydro-2H-pyridin-1-yl)-propyl]-1H-quinazoline-2,4-dione;

5-Methyl-3-[3-(6-methyl-3',6'-dihydro-2'H-[2,4']bipyridinyl-1'-yl)-propyl]-1H-quinazoline-2,4-dione;

3- {3-[4-(4-Chloro-phenyl)-3,6-dihydro-2H-pyridin-1-yl]-1-propyl}-1H-quinazoline-2,4-dione;

3-{3-[4-(1H-Pyrrolo[2,3-b]pyridin-3-yl)-3,6-dihydro-2H-pyridin-1-yl]-1-propyl}1H-quinazoline-2,4-dione;

3-{3-[4-(3-Trifluoromethyl-phenyl)-3,6-dihydro-2H-pyridin-1-yl]-1-propyl}1H-quinazoline-2,4-dione;

3-{3-[4-(3-Trifluoroacetyl-1H-indol-4-yl)-3,6-dihydro-2H-pyridin-1-yl]-1H-quinazoline-2,4-dione;

3-{3-[4-(5-Nitro-1H-indol-3-yl)-3,6-dihydro-2H-pyridin-1-yl]-1-propyl}-1H-quinazoline-2,4-dione;

7-Chloro-3-{3-[4-(4-Chloro-phenyl)-3,6-dihydro-2H-pyridin-1-yl]-1-propyl}-1-methyl-1H-quinazoline-2,4-dione;

and pharmaceutically acceptable salts of all of the foregoing.

Specifically, the most preferred embodiments of the present invention are:

3-{3-[4-(4-Chloro-phenyl)-3,6-dihydro-2H-pyridinyl-1-yl]-propyl}-6-methyl-1H-quinazoline-2,4-dione;

3-{3-[4-(4-Chloro-phenyl)-3,6-dihydro-2H-pyridinyl-1-yl]-propyl}-8methoxy-1H-quinazoline-2,4-dione;

3-{3-[4-(4-Chloro-phenyl)-3,6-dihydro-2H-pyridinyl-1-yl]-propyl}-8-chloro-1H-quinazoline-2,4-dione;

5-Methyl-3-[3-(4-m-tolyl-3,6-dihydro-2H-pyridin-1-yl)-propyl]-1H-quinazoline-2,4-dione;

3-{3-[4-(4-Chloro-phenyl)-3,6-dihydro-2H-pyridin-1-yl]-propyl}-5-fluoro-1H-quinazoline-2,4-dione;

3-{3-[4-(4-Chloro-phenyl)-3,6-dihydro-2H-pyridin-1-yl]-propyl}-6-fluoro-1H-quinazoline-1H-quinazoline-2,4-dione;

3-{3-[4-(4-Chloro-phenyl)-3,6-dihydro-2H-pyridin-1-yl]-propyl}-7-fluoro-1H-quinazoline-2,4-dione;

3-{3-[4-(4-Chloro-phenyl)-3,6-dihydro-2H-pyridin-1-yl]-propyl}-6,7-difluoro-1H-quinazoline-2,4-dione;

and pharmaceutically acceptable salts thereof.

As noted above, the present invention functions to inhibit serotonin reuptake and to inhibit 5-$HT_{2A}$ serotonin receptor binding in the central nervous system of a mammal, said method comprising the administration to a mammal of a serotonin reuptake-inhibiting effective amount or a serotonin receptor binding-inhibiting effective amount of a compound of formula (I) provided by this invention. Additionally provided herein is a method of treating a mammal afflicted with various diseases, disorders and conditions, said method comprising administering to the mammal a therapeutically effective amount of a compound of formula (I) of this invention.

A preferred method of treating diseases, disorders and conditions provided by this invention utilizes compounds of formula (I) wherein A is $(CH_2)_n$ where n is equal to 1 or 2, and U, V, W, X, Y, $R^1$, $R^2$, $R^3$, $R^4$, $R^5$, $R^6$ and $R^7$ are as defined above.

A further preferred method of treating diseases, disorders and conditions provided by this invention comprises the administration of a compound of formula (I) wherein n is equal to zero (i.e. without a bridging A group); W is C(=O); X is C; Y is C; V is CH or N; and U, $R^1$, $R^2$, $R^3$, $R^4$, $R^5$, $R^6$ and $R^7$ are as defined above.

A more preferred method of treating diseases, disorders and conditions provided by this invention comprises the administration of a compound of formula (I) wherein n is equal to zero (i.e. without a bridging A group); W is C(=O); X is C; Y is C; V is CH or N; U is NH, and $R^1$, $R^2$, $R^4$, $R^5$ are independently chosen from the group consisting of hydrogen, halo, —$CF_3$, nitro, $(C_1-C_6)$alkyl, hydroxy or methoxy.

A further more preferred method of treating diseases, disorders and conditions provided by this invention comprises the administration of a compound of formula (I) wherein n is equal to zero (i.e. without a bridging A group); W is C(=O); X is C; Y is C; V is CH; U is NH, and $R^1$, $R^2$, $R^4$, $R^5$ are independently chosen from the group consisting of hydrogen, halo, —$CF_3$, nitro, methyl, hydroxy or methoxy. Specifically, the more preferred method of treating diseases, disorders and conditions provided by this invention comprises the administration of one of the specifically disclosed more preferred embodiments of the compounds of formula (I) herein above.

The most preferred methods of treating disease, disorders and conditions provided by this invention comprises the administration of one of the specifically disclosed most preferred embodiments of the compounds of formula (I) herein above.

Further provided herein is a pharmaceutical composition comprising the compounds of this invention and a pharmaceutically acceptable carrier. Still further provided is a pharmaceutical composition for selectively inhibiting serotonin reuptake or serotonin receptor binding in the central nervous system (CNS) of a mammal, said composition comprising a pharmaceutically acceptable carrier and a serotonin reuptake-inhibiting effective amount or a serotonin receptor binding-inhibiting effective amount of the compound of this invention.

The present invention further provides methods for preparing compounds of formula (I), as set forth in Scheme I below, comprising the step of allowing a compound of formula (AII) to react with a compound of formula (BI), wherein A, n, m, U, V, W, X, Y, $R^1$, $R^2$, $R^3$, $R^4$, $R^5$, $R^6$ and $R^7$ are as described herein above.

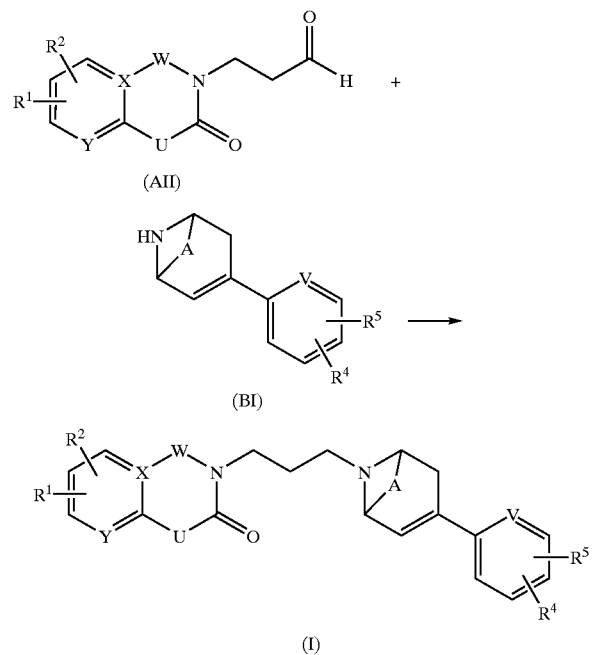

Scheme I

Preferred methods of the invention are those according to Scheme I wherein U is NH; V is CH or N; W is carbonyl; X is C; n is 0 (i.e., where there is no bridging group A); Y is C and m, Y, $R^1$, $R^2$, $R^3$, $R^4$, $R^5$, $R^6$ and $R^7$ are as defined above.

The present invention also relates to a method for the preparation of a compound of formula (1), as set forth in Scheme II below, comprising the steps of (a) allowing a compound of formula (AIII) to react with a compound of formula (BII) to form a compound of formula (CI) and (b) allowing a compound of formula (CI) to undergo a ring closure reaction to form a compound of formula (I), wherein in (AIII), (BII) and (CI), A, V, X, Y, $R^1$, $R^2$, $R^4$ and $R^5$ are as defined above; "Lower alkyl" means $(C_1-C_6)$alkyl, U is $CH_2$ or NH, and U' is N or CH.

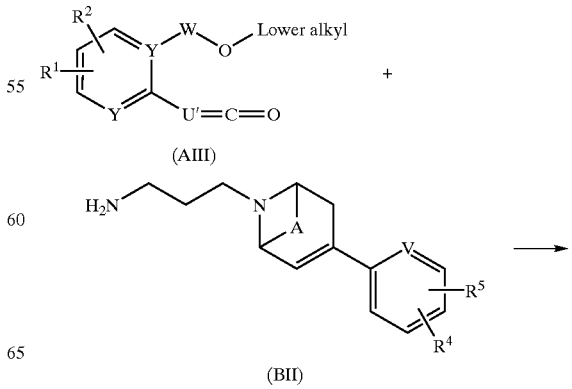

Scheme II

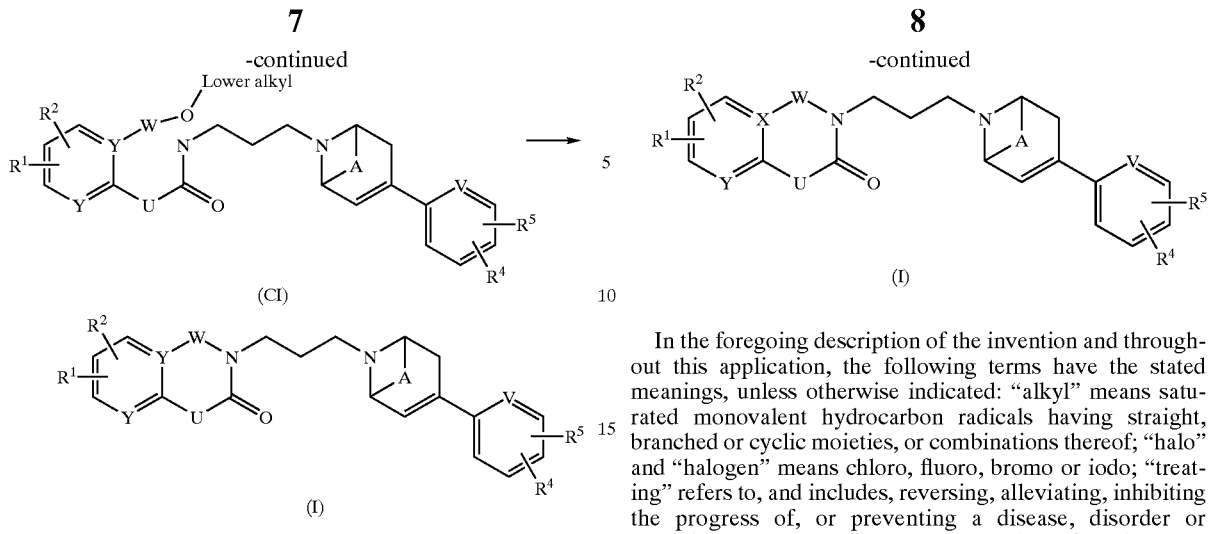

Other preferred methods of the invention are those methods represented by Scheme II, wherein U is NH, U' is N; V is CH or N; W is carbonyl; X is C; n is 0 (i.e., where there is no bridging group A); Y is C and m, Y, $R^1$, $R^2$, $R^3$, $R^4$, $R^5$, $R^6$ and $R^7$ are as defined above.

The present invention also relates to a method for the preparation of a compound of formula (I), as set forth in Scheme VI below, comprising the steps of (a) allowing a compound of formula (DIII) to react with a halopropylisocyanate compound to form a compound of formula (GI) and (b) allowing a compound of formula (GI) to undergo a double ring closure reaction to form a tricyclic compound of formula (FI), which is then (c) further reacted with a compound of formula (BI), or a salt thereof, to form compound of formula (1), wherein A, V, U, U', X, Y, $R^1$, $R^2$, $R^4$ and $R^5$ are as defined above.

Preferred methods of the invention relate to those represented in Scheme VI wherein U is NH, U' is N, V is CH, W is CO, X is C, n is 0 (where there is no bridging group A) and Y is C.

Scheme VI

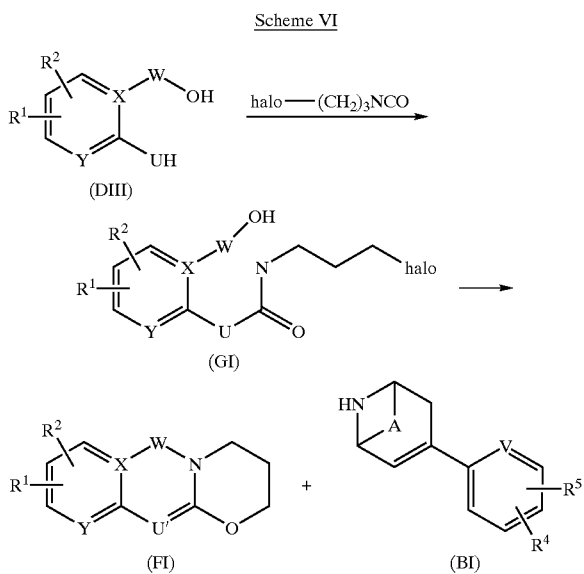

In the foregoing description of the invention and throughout this application, the following terms have the stated meanings, unless otherwise indicated: "alkyl" means saturated monovalent hydrocarbon radicals having straight, branched or cyclic moieties, or combinations thereof; "halo" and "halogen" means chloro, fluoro, bromo or iodo; "treating" refers to, and includes, reversing, alleviating, inhibiting the progress of, or preventing a disease, disorder or condition, or one or more symptoms thereof; and, "treatment" and "therapeutically" refer to the act of treating, as defined above.

"Serotonin receptor binding-inhibiting effective," "serotonin reuptake-inhibiting effective" and "therapeutically effective" amounts are each any amounts of compounds provided herein which are sufficient for inhibiting serotonin reuptake into presynaptic neurons, or serotonin binding to receptors in post-synaptic membranes, in the central nervous systems of mammals, including humans.

The various "diseases, disorders and conditions" to which the compositions and methods of this invention are directed include, without limitation: aggression disorders; anxiety disorders selected from the group consisting of panic attack, agoraphobia, panic disorder with or without agoraphobia, agoraphobia without history of panic disorder, specific phobia, social phobia, obsessive-compulsive disorder, post-traumatic stress disorder and acute stress disorder; cognitive disorders selected from the group consisting of amnestic disorders (e.g., amnestic disorders due to a general medical condition, substance-induced persisting amnestic disorder and amnestic disorders not otherwise specified), deliriums (e.g., deliriums due to a general medical condition, substance-induced delirium and delirium not otherwise specified), dementias (e.g., dementia of the Alzheimer's type, vascular dementia, dementia due to a general medical condition (e.g., AIDS-, Parkinson's-, head trauma-, and Huntington's-induced dementias), substance-induced persisting dementia, dementia due to multiple etiologies, and dementia not otherwise specified) and cognitive disorders not otherwise specified; depression disorders; emesis; epilepsy; food-related behavioral disorders, including anorexia nervosa and bulimia; headache disorders selected from the group consisting of migraine, cluster and vascular headaches; learning disorders, including attention deficit disorder and attention deficit/hyperactivity disorder; obesity; ocular disorders; platelet aggregation disorders; psychotic conditions selected from the group consisting of schizophrenia (e.g., paranoid-type, disorganized-type, catatonic-type, undifferentiated-type and residual-type), schizophreniform disorder, schizoaffective disorder, delusional disorder, brief psychotic disorder, shared psychotic disorder, psychotic disorders due to a general medical condition and psychotic disorders not otherwise specified; sleep disorders selected from the group consisting of primary sleep disorders (e.g., parasomnias and dyssomnias), sleep disorders related to another mental disorder (including, without limitation, mood and anxiety disorders), sleep disorders due to a general medical condition and sleep disorders not otherwise specified; sexual behavior disorders; substance-abuse disorders selected from the group consisting of alcohol-related disorders, including alcohol-use disorders (e.g., dependence and abuse disorders) and alcohol-induced disorders (e.g., intoxication, withdrawal, intoxication delirium, withdrawal delirium, persisting dementia, persisting amnestic, mood, anxiety, sexual dysfunction, sleep and not otherwise specified disorders), amphetamine-related disorders, including amphetamine-use disorders (e.g., dependence and abuse disorders) and amphetamine-induced disorders (e.g, intoxication, withdrawal, intoxication delirium, psychotic, mood, anxiety, sexual dysfunction, sleep and not otherwise-specified disorders), caffeine-related disorders, such as intoxication, induced-anxiety disorder, induced-sleep disorder and disorders not otherwise specified; cannabis-related disorders, including cannabis-use disorders (e.g., abuse and dependence disorders) and cannabis-induced disorders (e.g., intoxication, intoxication delirium, psychotic, anxiety and not otherwise specified disorders), cocaine-related disorders, including cocaine-use disorders (e.g., dependence and abuse disorders) and cocaine-induced disorders (e.g., intoxication, withdrawal, intoxication delirium, psychotic, mood, anxiety, sexual dysfunction, sleep and not otherwise specified disorders), hallucinogen-related disorders, including hallucinogen-use disorders (e.g., dependence and abuse disorders) and hallucinogen-induced disorders (e.g., intoxication, persisting perception, intoxication delirium, psychotic, mood, anxiety and not otherwise specified disorders), inhalant-related disorders, including inhalant-use disorders (e.g., dependence and abuse disorders) and inhalant-induced disorders (e.g., intoxication, intoxication delirium, persisting dementia, psychotic, mood, anxiety and not otherwise specified disorders), nicotine-related disorders, such as dependence, withdrawal and not otherwise specified disorders, opioid related disorders, including opioid-use disorders (e.g., dependence and abuse disorders) and opioid-induced disorders (e.g., intoxication, withdrawal, intoxication delirium, psychotic, mood, sexual dysfunction, sleep and not otherwise-specified disorders), phencyclidine-related disorders, including phencyclidine-use disorders (e.g., dependence and abuse disorders) and phencyclidine-induced disorders (e.g., intoxication, intoxication delirium, psychotic, mood, anxiety and not otherwise-specified disorders), sedative-, hypnotic- or anxiolytic-related disorders, including sedative-use disorders (e.g., dependence and abuse disorders) and sedative-induced disorders (e.g., intoxication, withdrawal, intoxication delirium, withdrawal delirium, persisting dementia, persisting amnestic, psychotic, mood, anxiety, sexual dysfunction, sleep and not otherwise specified disorders), polysubstance-related disorder, other substance dependence and abuse disorders, and other substance-induced disorders (e.g, intoxication, withdrawal, delirium, persisting dementia, persisting amnestic, psychotic, mood, anxiety, sexual dysfunction, sleep and not otherwise specified disorders); vision disorders, including glaucoma; and, various additional diseases, disorders and conditions as well.

"Pharmaceutically acceptable salts" or "pharmaceutically acceptable acid addition salts" of compounds of this invention may be made from those acids which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (ie., 1,1-methylene-bis-(2-hydroxy-3-naphthoate)salts.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Although such salts must be pharmaceutically acceptable for administration to animals, it is often desirable in practice to initially isolate a compound of the formula I from the reaction mixture as a pharmaceutically unacceptable salt, convert the latter back to the free base compound by treatment with an alkaline reagent, and subsequently convert the latter free base to a pharmaceutically acceptable acid addition salt. Such salts are readily prepared by treating the base compound with a substantially equivalent amount of the chosen mineral or organic acid in an aqueous solvent medium, or in a suitable organic solvent, such as methanol or ethanol. Upon careful evaporation of the solvent, the desired solid salt is readily obtained.

The compounds of this invention and their pharmaceutically acceptable salts are useful as selective serotonin reuptake inhibitors and 5-$HT_{2A}$ receptor binding inhibitors. Therefore, said compounds are able to function as therapeutic agents in mammals, including humans, afflicted with various diseases, disorders and conditions, such as those set forth above, characterized by aberrant behavior of the serotonin neurotransmission system.

Compounds of formula (I) may contain chiral centers, and therefore may exist in different enantiomeric and diastereomeric forms; this invention is directed to all such optical and stereoisomers of compounds of formula (I), as well as mixtures thereof, and to all pharmaceutical compositions and methods of treatment that contain or employ them.

This invention is also directed to isotopically-labeled compounds identical to those recited in formula (I), or pharmaceutically acceptable salts thereof, but for the fact that one or more atoms are replaced therein by an atom having an atomic mass or mass number different from the atomic mass or mass number usually found in nature. Examples of isotopes that can be incorporated into compounds of this invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

Compounds of the present invention, prodrugs thereof, and pharmaceutically acceptable salts of said compounds, or of said prodrugs, which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful, for example, in drug and/or substrate tissue distribution assays. Tritiated, i.e., $^3H$, and carbon-14, i.e., $^{14}C$, isotopes are particularly preferred for their ease of preparation and detectability. Furthermore, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances.

Isotopically labeled compounds of formula (I) of this invention and prodrugs thereof can generally be prepared by carrying out the procedures set forth below, by substituting a readily available isotopically labeled reagent for a non-isotopically labeled reagent.

DETAILED DESCRIPTION OF THE INVENTION

Compounds of formula (I) may be prepared as described below, wherein, unless otherwise indicated, U, V, W, X, Y, $R^1$, $R^2$, $R^3$, $R^4$, $R^5$, $R^6$, $R^7$ and the structural formula (I) in the discussion that follows are as defined above. Compounds of the formula (I) may be prepared by processes as set forth below in Schemes Ia and IIa:

Scheme Ia

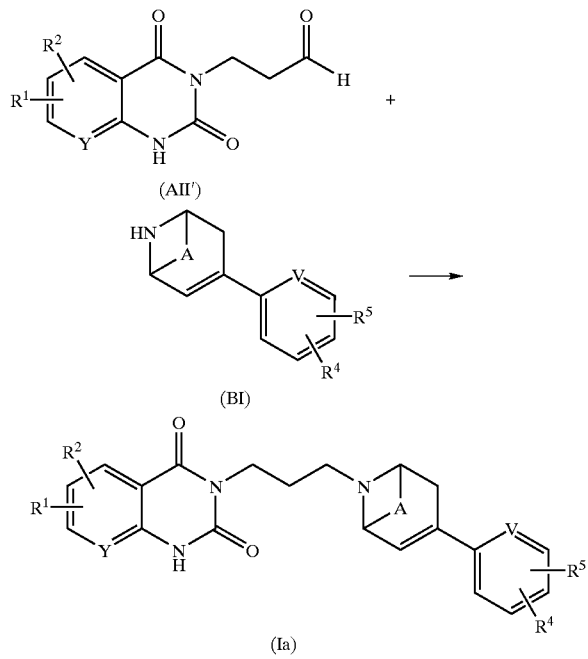

Scheme IIa

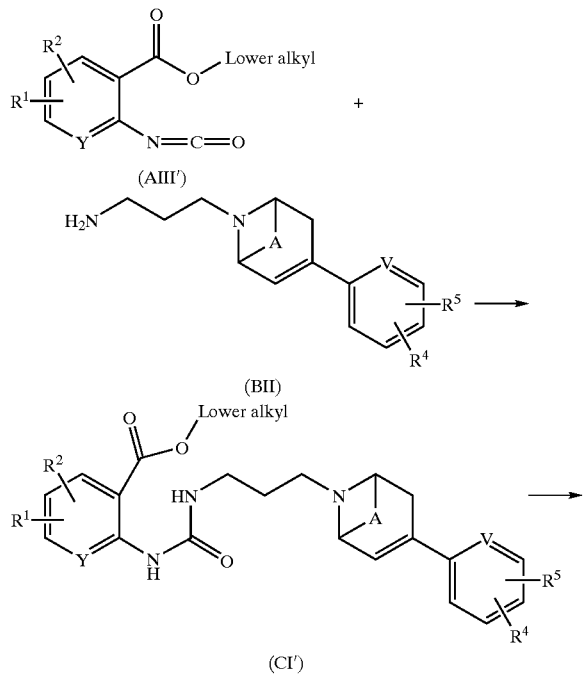

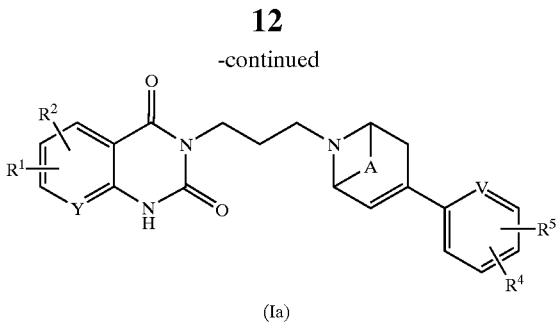

In Scheme Ia, compounds of formula (I) and (Ia) are prepared by reacting a compound of the general formula (AII') with a compound of the general formula (BI), wherein V, Y, $R^1$, $R^2$, $R^3$, $R^4$, $R^5$, $R^6$ and $R^7$ are as defined above. The reaction of Scheme Ia may be carried out in any reaction inert solvent, which does not interact with the starting materials, reagents, intermediates or products in a manner which adversely affects the yield of the desired product, such as alcohols, cyclic and acyclic mono- and dialkylamides, acetonitrile, cyclic and acyclic alkyl ethers, or aromatic solvents (e.g., benzene, toluene, etc.), at a temperature in the range of 0° C. to 150° C. The general reaction of Scheme I may be carried out analogously under the same reaction conditions where A, n, U, V, W, X, Y, $R^1$, $R^2$, $R^3$, $R^4$, $R^5$, $R^6$ and $R^7$ are as defined above.

A compound of the general formula (AII) utilized in the reaction of Scheme I is readily prepared from a compound of the general formula (AI):

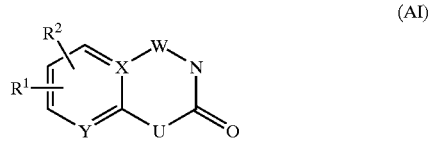

wherein U, W, X, Y, $R^1$, and $R^2$ are as defined above, by allowing it to react with an appropriate α,β-unsaturated aldehyde or ketone derivatives in a suitable solvent, e.g., in combinations of cyclic or acyclic monoalkylamides or dialkylamides and $C_1$–$C_4$ alcohols, at reaction temperatures of 0–150° C., more preferably either at about 0° C. or near the boiling point of the solvent mixture used. The presence of acid acceptors, e.g., alkali carbonates, tertiary amines et al., is often helpful in such reactions may be either obtained from commercial sources or are prepared from known and readily available materials.

As shown in Scheme III, compounds of the general formula (BI) are, for example, prepared by reacting readily prepared or commercially available piperidine-4-one compounds of the general formula EIB), wherein $R^8$ denotes a nitrogen-protecting group, with an aryl or heteroaryl group transferring reagent of the general formula EIA), wherein M denotes a metal ion, such as $Li^+$, $Mg^{2+}$, etc. and V, $R^3$ and $R^4$ are as defined above, to provide intermediates of the general formula DI.

Scheme III

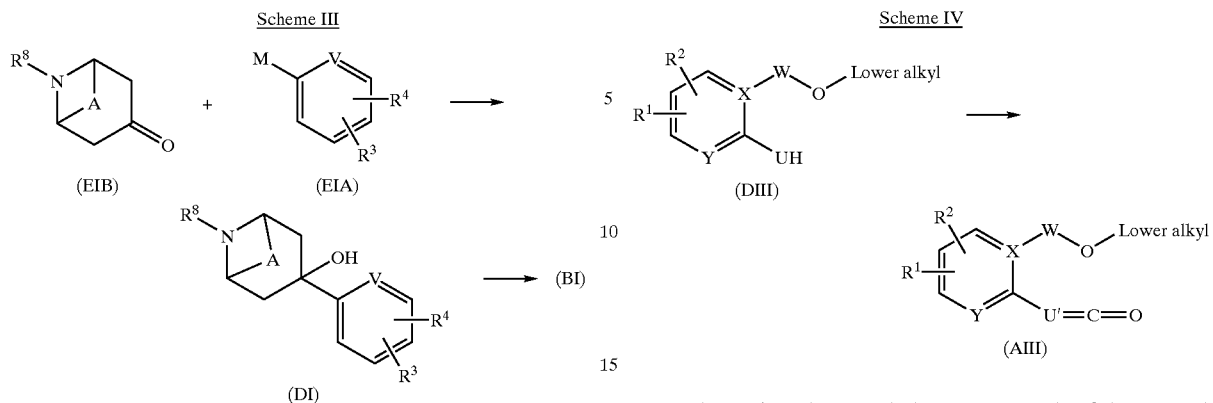

Compounds of the general formula (DI) may then be converted into compounds of formula (BI) via conventional dehydration procedures, e.g., reaction with an alkyl or aralkyl sulfonic acid, or a mineral acid, in solvent mixtures comprising, for example, cyclic and acyclic alkyl ethers, cyclic and acyclic alkyl esters, cyclic and acyclic alkyl ketones, pyridine derivatives, halogenated solvents or cyclic and acyclic N-,N-dialkyl alkylamides, at temperatures of first from about −40° C. to about 0° C., and then from about 0° C. to about 150° C., then followed by removal of the nitrogen-protecting group. Protecting groups on the nitrogen atoms of compounds (EIB) and (DI) are any of those protecting groups commonly known and used for such reactions, including, e.g., benzyl, benzyloxycarbonyl, t-butoxycarbonyl, trityl groups et al. It is often convenient to remove such groups by readily practiced hydrogenation or acidic procedures readily known in the art. see, T. W. Greene and G. M. Wuts, *Protective Groups in Organic Synthesis* (J. Wiley & Sons, New York 1991).

Specific embodiments of the invention may also be prepared in accordance with reaction Scheme IIa. In Scheme IIa, a compound of formula (Ia) is prepared by permitting the reaction of a compound of the general formula (AIII'), wherein Y, $R^1$ and $R^2$ are as defined above and "Lower alkyl" means $(C_1-C_6)$alkyl, with a compound of the general formula (BII), wherein V, $R^4$ and $R^5$ are as defined above, to provide an intermediate compound of the general formula (CI'). A compound of formula (Ia) is formed via a ring closure of intermediate (CI'). The steps of this reaction may be carried out in any reaction inert solvent, which does not interact with the starting materials, reagents, intermediates or products in a manner which adversely affects the yield of the desired product, such as alcohols, cyclic and acyclic mono- and dialkylamides, acetonitrile, cyclic and acyclic alkyl ethers, or aromatic solvents (e.g., benzene, toluene, etc.), at a temperature in the range of 0° C. to 150° C. The intermediate compound (CI') may be isolated or further permitted to undergo the ring closure reaction in the same reaction vessel/mixture.

As shown in Scheme IV below, compounds of the general formula (AIII) are, for example, prepared by reacting a compound of the general formula (DIII), with triphosgene, or an equivalent thereof, such as carbonyl diimidazole, phosgene or the like, in the presence of a base such as a tertiary amine in various combinations of inert organic solvents, e.g., cyclic and acyclic alkyl ethers, cyclic and acyclic alkyl esters, cyclic and acyclic alkyl ketones, pyridine derivatives and halogenated solvents. Reaction temperatures are preferably first about 0° C., and then are about the boiling point of the solvent combination used.

Scheme IV

As shown in Scheme V below, compounds of the general formula BII are, for example, prepared by reacting a compound of the general formula BI with an amino propyl transferring agent of the general formula EII, thereby providing compounds of the general formula DII, from which the protecting groups are then removed so as to arrive at the compounds BII. Such reactions are, for example, conducted in solvents, or solvent combinations, such as alcohols, cyclic and acyclic alkyl esters, cyclic and acyclic alkyl ketones, cyclic and acyclic mono- and dialkylamides, acetonitrile or cyclic and bicyclic alkyl ethers; the presence of an acid acceptor, e.g., an alkali carbonate or tertiary amine, is often useful. When protecting groups, such as benzyl, benzyloxycarbonyl, t-butoxycarbonyl, or trityl groups are employed, it is often convenient to remove such groups using readily practiced hydrogenation or acidic procedures; other commonly used protecting groups are also introduced and removed using well known, and readily practiced, techniques.

Scheme V

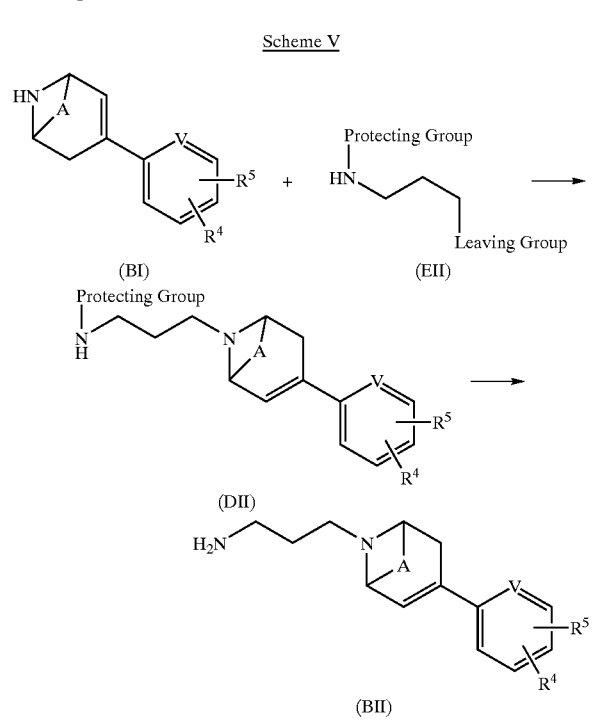

Suitable leaving groups are those leaving groups that would be well known to one of skill in the art, e.g., mesylate, tosylate, etc.

Another more preferred method for preparing compounds of formula (I) proceeds via reaction Scheme VIa below.

Scheme VIa

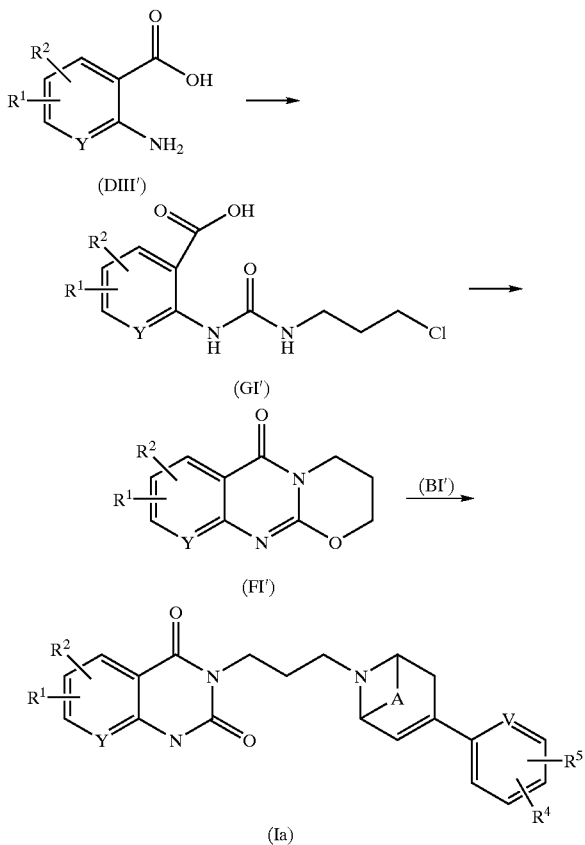

Compounds of formula (Ia) may be prepared by reacting a compound of formula (DIII') via reaction with a halopropylisocyanate, e.g., chloropropylisocyanate, to arrive at the corresponding ureido compound (GI') which is then further reacted, either after isolation or in the same reaction mixture, with a base or acid acceptor to form the tricyclic compound (FI'). The tricyclic (FI') is then converted to a compound of formula (I) via heating with the salt (BI'), e.g., hydrochloride salt, etc., of the tetrahydropyridine compound (BI). The steps of reaction Scheme VIa may be all be conducted in the presence of an acid acceptor, e.g., an alkali carbonate, bicarbonate, tertiary amine, etc. in a solvent system such as that described above for Scheme IV.

The preparation of other compounds of formula (I) not specifically described in the foregoing section can be accomplished using combinations of the reactions described above that will be apparent to those skilled in the art. Furthermore, in each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred, as a matter of convenience.

Serotonin receptor binding affinities of compounds of formula (I) can be determined using standard radioligand binding assays as described in the literature. For example, 5-$HT_{1A}$ receptor binding affinities can be measured using the procedure of Hoyer et al. (*Brain Res.*, 376:85 (1986)), and 5-$HT_{1D}$ binding affinities can be measured using the procedure of Heuring and Peroutka (*J. Neurosci.*, 7:894 (1987)); the contents of these documents are incorporated herein by reference.

In vitro binding activity at the 5-$HT_{1D}$ receptor binding site is, for example, determined according to the following procedure. Bovine caudate tissue is homogenized and suspended in 20 volumes of a buffer containing 50 mM TRIS-HCl (tris[hydroxymethyl]aminomethane hydrochloride) at a pH of 7.7, following which the homogenate is centrifuged at 45,000 g for 10 minutes. The resulting supernatant is discarded, and the pellet is resuspended in approximately 20 volumes of 50 mM TRIS-HCl buffer at pH 7.7; said suspension is pre-incubated for 15 minutes at 37° C., after which it is centrifuged again at 45,000 g for 10 minutes. The resulting supernatant discarded, and the pellet (approximately 1 gram) is resuspended in 150 ml of a buffer of 15 mM TRIS-HCl containing 0.01 percent ascorbic acid, final pH 7.7, 10 µM pargyline and 4 mM calcium chloride ($CaCl_2$)—the suspension is kept on ice at least 30 minutes prior to use.

The inhibitor, control or vehicle is incubated according to the following procedure: to 50 µl of a 20 percent dimethylsulfoxide (DMSO)/80 percent distilled water solution is added 200 µl of tritiated 5-hydroxytryptamine (2 nM) in a buffer of 50 mM TRIS-HCl containing 0.01 percent ascorbic acid at pH 7.7, 10 µM pargyline, 4 mM calcium chloride, 100 nM of 8-hydroxy-DPAT (dipropylaminotetraline) and 100 nM of mesulergine. To this mixture is added 750 µl of bovine caudate tissue, and the resulting suspension is vortexed to ensure a homogenous suspension; the suspension is then incubated in a shaking water bath for 30 minutes at 25° C.; after incubation is complete, the suspension is filtered using glass fiber filters (e.g., Whatman GF/B-filters). The pellet is washed three times with 4 ml of a buffer of 50 mM TRIS-HCI (pH 7.7), and is then placed in a scintillation vial with 5 ml of scintillation fluid (aquasol 2) and allowed to sit overnight. The percent inhibition is calculated for each dose of the compound, and an $IC_{50}$ value is then calculated from the percent inhibition values.

Binding affinities at the 5-$HT_{1A}$ receptor is, for example, determined according to the following procedure. Rat brain cortex tissue is homogenized and divided into samples of 1 g lots and diluted with 10 volumes of 0.32 M sucrose solution. The suspension is then centrifuged at 900 g for 10 minutes, the supernatant separated and recentrifuged at 70,000 g for 15 minutes and the pellets are then collected and resuspended in 10 volumes of 15 mM TRIS-HCl (pH 7.5); the remaining supernatant is discarded. The resulting suspension is allowed to incubate for 15 minutes at 37° C., after which it is then centrifuged at 70,000 g for 15 minutes and the supernatant discarded. The resulting tissue pellet is resuspended in a buffer of 50 mM TRIS-HCl (pH 7.7) containing 4 mM of calcium chloride and 0.01 percent ascorbic acid—this tissue suspension is stored at −70° C. until ready for an experiment.

The tissue can be thawed immediately prior to use, diluted with 10 µM pargyline and kept on ice; tissue incubation is according to the following procedure. Fifty microliters of control, inhibitor, or vehicle (1 percent DMSO final concentration) is prepared at various dosages. To this solution is added 200 µl of tritiated 8-hydroxy DPAT at a concentration of 1.5 nM in a buffer of 50 mM TRIS-HCl at pH 7.7, containing 4 mM calcium chloride, 0.01 percent ascorbic acid and pargyline. 750 µl of tissue is added, the resulting suspension is vortexed to ensure homogeneity, and is then incubated in a shaking water bath for 30 minutes at 37° C. The solution is filtered, and then washed twice with 4 ml of 10 mM TRIS-HCl at pH 7.5 containing 154 mM of sodium chloride.

Agonist and antagonist activities of compounds of formulae (I) at the 5-$HT_{1A}$ and 5-$HT_{1D}$ receptors is, for example, determined using a single saturating concentration according to the following procedure. Male Hartley guinea pigs are decapitated and 5-$HT_{1A}$ receptors are dissected out of the hippocampus, while 5-$HT_{1D}$ receptors are obtained by slicing at 350 mm on a McIlwain tissue chopper and dissecting out the substantia nigra from the appropriate slices. The individual tissues are homogenized in a 5 mM HEPES buffer containing 1 mM EGTA (pH 7.5) using a hand-held glass-Teflon® homogenizer and centrifuged at 35,000 g for 10 minutes at 4° C. The resulting pellets are resuspended in a 100 mM HEPES buffer containing 1 mM EGTA (pH 7.5), to a final protein concentration of 20 mg (hippocampus) or 5 mg (substantia nigra) of protein per tube; the following agents are added so that the reaction mix in each tube contains 2.0 mM $MgCl_2$, 0.5 mM ATP, 1.0 mM cAMP, 0.5 mM IBMX, 10 mM phosphocreatine, 0.31 mg/mL creatine phosphokinase, 100 μM GTP and 0.5–1 microcuries of [$^{32}$P]-ATP (30 Ci/mmol: NEG-003—New England Nuclear). Incubation is initiated by the addition of tissue to siliconized microfuge tubes (in triplicate) at 30° C. for 15 minutes. Each tube receives 20 μl tissue, 10 μl drug or buffer (at 10× final concentration), 10 μl of 32 nM agonist or buffer (at 10× final concentration), 20 μl forskolin (3 μM final concentration) and 40 μl of the preceding reaction mix. Incubation is terminated by the addition of 100 μl 2% SDS, 1.3 mM cAMP, 45 mM ATP solution containing 40,000 dpm [$^{3}$H]-cAMP (30 Ci/mmol: NET-275—New England Nuclear) to monitor the recovery of cAMP from the columns (the separation of [$^{32}$P]-ATP and [$^{32}$P]-cAMP is accomplished using the method of Salomon et al., *Analytical Biochemistry*, 58:541–548 (1974), the contents of which are incorporated herein by reference). Radioactivity is quantified by liquid scintillation counting. Maximal inhibition is defined by 10 μM (R)-8-OH-DPAT for 5-$HT_{1A}$ receptors, and 320 nM 5-HT for 5-$HT_{1D}$ receptors. Percent inhibitions by the test compounds are then calculated in relation to the inhibitory effect of (R)-8-OH-DPAT for 5-$HT_{1A}$ receptors or 5-HT for 5-$HT_{1D}$ receptors. The reversal of agonist-induced inhibition of forskolin-stimulated adenylate cyclase activity is calculated in relation to the 32 nM agonist effect.

The compounds of this invention are, for example, tested for in vivo activity for antagonism of 5-$HT_{1D}$ agonist-induced hypothermia in guinea pigs according to the following procedure. Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing. Compounds of formula (I) are administered, for example, as solutions in a volume of 1 ml/kg; the vehicle used is varied depending on compound solubility. Test compounds are typically administered either sixty minutes orally (p.o.) or 0 minutes subcutaneously (s.c.) prior to administration of a 5-$HT_{1D}$ agonist, such as [3-(1-methylpyrrolidin-2-ylmethyl)-1H-indol-5-yl]-(3-nitropyridin-3-yl)-amine, which can be prepared as described in PCT publication WO93/111 06, published Jun. 10, 1993 (the contents of which are incorporated herein by reference), and which is administered at a dose of 5.6 mg/kg, s.c.

Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-$HT_{1D}$ agonist is then administered at 0 minutes and temperatures are taken 30, 60, 120 and 240 minutes later. In subcutaneous screening experiments, a pre-drug baseline temperature reading is made at −30 minutes. The test compound and 5-$HT_{1D}$ agonists are given concurrently and temperatures are taken at 30, 60, 120 and 240 minutes later. Data are analyzed with two-way analysis of variants with repeated measures in Newman-Keuls post hoc analysis.

The serotonin 5-$HT_1$ agonist activity can be determined by in vitro receptor binding assay, as described for the 5-$HT_{1A}$ receptor using rat cortex as the receptor source and [$^{3}$H]-8-OH-DPAT as the radioligand [D. Hoyer et al. *Eur. J. Pharm.*, 118, 13 (1985)] and as described for the 5-$HT_{1D}$ receptor using bovine caudate as the receptor source and [$^{3}$H]serotonin as the radioligand [R. E. Heuring and S. J. Peroutka, *J. Neuroscience*, 7, 894 (1987)]; the contents of these documents are incorporated herein by reference.

The binding activity at the 5-$HT_{2A}$ receptor is, for example, determined according to the following procedure. Male Sprague-Dawley rats are decapitated and their brains removed. Frontal cortices are dissected and homogenized in 50 mM Tris HCl buffer (pH 7.4 at 4° C.) containing 2 mM MgCl2 using a Polytron homogenizer (setting 15,000 rpm). The homogenate is centrifuged for ten minutes at 40,000×g (20,000 rpm in a Sorvall SS34 rotor). The supernatant was discarded and the pellet resuspended with the Polytron homogenizer in fresh ice-cold 50 mM TRIS HCl (pH 7.4 at 4° C.) buffer containing 2 mM MgCl2 and centrifuged again. The final pellet was resuspended in 50 mM Tris HCl buffer (pH 7.7 at 22° C.) for a final tissue concentration of 9 mgs wet weight tissue per mL buffer. Incubation is initiated by the =addition of tissue to V-bottom polypropylene 96 well plates (in triplicate). Incubation is at 37° C. for 15 minutes in a water bath. Each tube receives 200 μL tissue suspension, 25 μL $^{3}$H-ketanserin (0.4 nM final concentration), and 25 μL drug or buffer. Nonspecific binding is determined using 10 μM cinanserin. Incubation is ended by rapid filtration under vacuum through fire-treated Whatman GF/B glass fiber filters (presoaked in 0.5% polyethenylenimine (PEI) and dried) and rinsed with icecold 50 mM Tris HCl buffer (pH 7.7 at 4° C.), setting 555 on a Skatron 96 well harvester. Filters are put into sample bags with 10 mL Betaplate scintillation fluid and allowed to sit 10 minutes before counting on a Betaplate scintillation counter (Wallac).

The binding activity at the $\alpha_1$ receptor is, for example, determined according to the following procedure. Male Sprague-Dawley rats are decapitated and their brains removed. Cortices are dissected and homogenized in 50 mM Tris HCl buffer (pH 7.4 at 4° C.) containing 2 mM MgCl2 using a Polytron homogenizer (setting 15,000 rpm). The homogenate is centrifuged for ten minutes at 40,000×g (20,000 rpm in Sorvall SS34 rotor). The supernatant was discarded and the pellet resuspended with the Polytron homogenizer in fresh ice-cold 50 mM TRIS HCl (pH 7.4 at 4° C.) buffer containing 2 mM MgCl2 and centrifuged again. The final pellet was resuspended in 50 mM Tris HCl buffer (pH 8.0 at 22° C.) for a final tissue concentration of 12.5 mgs wet weight tissue per mL buffer. Incubation is initiated by the addition of tissue to V-bottom polypropylene 96 well plates (in triplicate). Incubation is at 25° C. for 30 minutes on a shaker. Each tube receives 200 μL tissue suspension, 25 μL 3 H-Prazosin (0.2 nM final concentration) and 25 μL drug or buffer. Nonspecific binding is determined using 10 μM phentolamine. Incubation is ended by rapid filtration under vacuum through fire-treated Whatman GF/B glass fiber filters (presoaked in 0.5% PEI and dried) and rinsed with ice-cold 50 mM Tris HCl buffer (pH 7.7 at 4° C.), setting 555 on a Skatron 96 well harvester. Filters are put into sample bags with 10 mL Betaplate scintillation fluid and allowed to sit 10 minutes before counting on a Betaplate scintillation counter (Wallac).

The binding activity at the dopamine $D_2$ receptor is, for example, determined according to the following procedure. Male Sprague-Dawley rats are decapitated and their brains removed. Striata are dissected and homogenized in 50 mM Tris HCl buffer (pH 7.4 at 4° C.) containing 2 mM $MgCl_2$ using a Polytron homogenizer (setting 15,000 rpm). The homogenate is centrifuged for ten minutes at 40,000×g (20,000 rpm in a Sorvall SS34 rotor). The supernatant was discarded and the pellet resuspended with the Polytron in fresh ice-cold 50 mM Tris HCl (pH 7.4 at 4° C.) containing 2 mM $MgCl_2$ buffer and centrifuged again. The final pellet was resuspended in 50 mM Tris HCl buffer containing 100 mM NaCl, 1 mM $MgCl_2$ (pH 7.4 at 37° C.) for a final tissue concentration of 3 mg wet weight tissue per mL buffer. Incubation is initiated by the addition of tissue to V-bottom polypropylene 96 well plates (in duplicate or triplicate). Incubation is at 37° C. for 15 minutes in a heated water bath. Each tube receives 200 μL tissue suspension, 25 μL $^3$H-spiperone (0.2 nM final concentration) and 25 μL drug or buffer. Nonspecific binding is determined using 10 μM (+)-butaclamol. Incubation is ended by rapid filtration under vacuum through fire-treated Whatman GF/B glass fiber filters (presoaked in 0.5% PEI and dried) and rinsed with ice-cold 50 mM Tris HCl buffer (pH 7.7 at 4° C.), setting 555 on the Skatron 96 well harvester (15 sec wash). Filters are dried, put into sample bags with 10 mL Betaplate scintillation fluid and counted on a Betaplate scintillation counter (EG&G/Wallac).

The neurotransmitter uptake activity in rat synaptosomes or HEK-293 cells transfected with the human serotonin, dopamine or norepinephrine transporter is, for example, determined according to the following procedure. For rat synaptosomes preparation, male Sprague Dawley rats are decapitated and the brains removed. The cortex, hippocampi and corpus striata are dissected out and placed in ice cold sucrose buffer, 1 gram in 20 mls (320 mM sucrose containing 1 mg/ml glucose, 0.1 mM EDTA and brought up to pH 7.4 with Tris base). The tissues are homogenized in a glass homogenizing tube with a teflon pestle at 350 RPMS using a Potters homogenizer. The homogenate is centrifuged at 1000×g for 10 min, at 4° C. The resulting supernatant is re-centrifuged at 17,000×g for 20 min, at 4° C. The final pellet is then resuspended in an appropriate volume of sucrose buffer that yielded less than 10% uptake.

For cell preparation, HEK-293 cells transfected with the human serotonin (5-HT), norepinephrine (NE) or dopamine (DA) transporter were grown in DMEM (Gibco) supplemented with 10% dialyzed FBS (Gibco), 2 mM L-glutamine and 250 μg/ml G418 for the 5-HT and NE transporter or 2 μg/ml puromycin for the DA transporter, for selection pressure. The cells were grown in Gibco triple flasks, harvested with PBS and diluted to an appropriate amount to yield less than 10% uptake.

For the neurotransmitter uptake assay, the uptake assays were conducted in glass tubes containing 50 μL of solvent, inhibitor or 10μM sertraline, desipramine or nomifensine for the 5-HT, NE or DA assay nonspecific uptake, respectively. Each tube contained 400 μL of [$^3$H]5-HT (5 nM final), [$^3$H]NE (20 nM final) or [$^3$H]DA (5 nM final) made up in modified Krebs containing 100 μM pargyline and glucose (1 mg/ml). The tubes were placed on ice, 50 μL of synaptosomes or cells was added to each tube. The tubes were then incubated at 37° C. for the 7 min (5-HT, DA) or 10 min (NE). The incubation was terminated by filtration (GF/B filters), using a 96 well Brandel Cell Harvester, the filters were washed with modified Krebs buffer and either counted in a liquid scintillation counter or in a LKB Beta Plate counter.

Compounds prepared as working examples of the present invention and tested in accordance with the foregoing methods showed good binding activity in the range of more than 50% inhibition at <50 (fifty) nm concentration in the serotonin reuptake assay and binding assays for 5-$HT_{2A}$ serotonin receptor while having an affinity of >100 (one hundred) nm at the dopamine D2 receptor, 5-$HT_{1A}$ serotonin, 5-$HT_{1D}$ or $α_1$ adrenergic receptor.

The compounds of this invention, and their pharmaceutically acceptable salts, can be administered via either the oral, parenteral or topical routes. In general, these compounds are most desirably administered in dosages ranging from about 0.01 to about 250 mg per day, in single or divided doses (e.g., from 1 to 4 doses per day), although variations will necessarily occur depending upon the species, weight and condition of the subject being treated, as well as the particular route of administration chosen. However, a dosage level that is in the range of about 0.07 mg to about 21 mg per kg of body weight per day is most desirably employed. Variations may nevertheless occur depending upon the subject being treated and its individual response to said medicament, as well as on the type of pharmaceutical formulation chosen, and the time period, and interval, at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants, such as starch (and preferably corn, potato or tapioca starch), alginic acid and certain complex silicates, and granulation binders, such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of formula I or II in either sesame or peanut oil, or in aqueous propylene glycol, may be employed. The aqueous solutions should be suitably buffered (preferably at a pH of greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically for the treatment of conditions of the skin; this may be done by way of creams, jellies, gels, pastes, patches, ointments and the like, in accordance with standard pharmaceutical practice.

EXAMPLES

The present invention is illustrated by the following examples. It will be understood, however, that the invention is not limited to the specific details of these examples. Melting points are uncorrected. Proton nuclear magnetic resonance spectra ($^1$H NMR) and $^{13}$C nuclear magnetic resonance spectra were measured using standard techniques. The peak shapes are denoted as follows: s, singlet; d, doublet; t, triplet; q, quartet; m, multiplet, b, broad.

Example 1

Preparation of 2,2,2-Trifluoro-N-(3-hydroxypropyl)-acetamide

3-Amino-1-propanol (10.0 mL, 0.131 mol) and methyl trifluoroacetate (65 mL, 0.646 mol) in methanol (200 mL) were refluxed for 1.5 h, cooled and concentrated to give 2,2,2-trifluoro-N-(3-hydroxypropyl)-acetamide (22.87 g, quantitative) as a light yellow oil which was used without purification. NMR CDCl$_3$ δ 7.45 (br s, 1H), 3.77 (t, J=5.5 Hz, 2H), 3.53–3.42 (m, 2H), 2.45 (s, 1H), 1.83–1.75 (m, 2H).

Example 2

Preparation of Methanesulfonic acid 3-(2,2,2-trifluoroacetylamino)-propyl ester

A solution of 2,2,2-trifluoro-N-(3-hydroxypropyl)-acetamide (2.00 g, 11.69 mmol) and triethylamine (1.7 mL, 12.2 mmol) in methylene chloride (35 mL) was cooled in an ice bath and methanesulfonic acid anhydride in methylene chloride (15 mL) was added dropwise over 1 minutes. After stirring for 45 minutes. at 0° C. the reaction was concentrated, the residue was partitioned between ether and water, the organic extractions were washed with brine and dried over magnesium sulfate. Concentration yielded methanesulfonic acid 3-(2,2,2-trifluoroacetylamino)-propyl ester.

Example 3

Preparation of N-{3-[4-(4-Chloro-phenyl)-3,6-dihydro-2H-pyridin-1-yl]-propyl}2,2,2-trifluoro-acetamide Methanesulfonic acid 3-(2,2,2-trifluoroacetylamino)-propyl ester (4.51 g, 18.10 mmol), 4-(4-chlorophenyl)-1,2,3,6-tetrahydropyridine hydrochloride (4.20 g, 18.25 mmol) and triethylamine (5.6 mL, 40.2 mmol) in ethanol (100 mL) were refluxed for 18 hours. The mixture was concentrated, redissolved in ethyl acetate and washed with saturated sodium bicarbonate and brine, dried over magnesium sulfate and concentrated on to silica gel. Flash chromatography using first an ethyl acetate/hexanes gradient followed by 3% methanol/ethyl acetate gave N-{3-[4-(4-chloro-phenyl)-3,6-dihydro-2H-pyridin-1-yl]-propyl}-2,2,2-trifluoro-acetamide (2.82 g, 45%) as a white solid. Mp. 105–107° C.; NMR CDCl$_3$ δ 9.58 (br s, 1H), 7.27–7.24 (m, 4H), 6.01–5.98 (m, 1H), 3.49 (g, J=5.3 Hz, 2H), 3.20–3.17 (m, 2H), 2.77 (t, J=5.7 Hz, 2H), 2.73–2.69 (m, 2H), 2.55–2.51 (m, 2H), 1.80 (p, J=3.6 Hz, 2H); $^{13}$C NMR CDCl$_3$ δ 138.80, 134.41, 133.15, 128.52, 126.22, 120.99, 57.72, 52.80, 50.15, 40.96, 27.61, 23.23; IR (KBr) 3300, 3099, 2981, 2953, 2925, 2907, 2810, 2758, 2734, 1695, 1558, 1494, 1469, 1444, 1352, 1184, 1137, 1118, 1097,801,722,692.

Example 4

Preparation of 3-[4-(4-Chloro-phenyl)-3,6-dihydro-2H-pyridin-1-yl]-propylamine

N-{3-[4-(4-Chloro-phenyl)-3,6-dihydro-2H-pyridin-1-yl]-propyl}-2,2,2-trifluoroacetamide (1.77 g, 5.10 mmol) and 20% aqueous KOH (25 mL) in ethanol (50 mL) were stirred at room temperature for 30 minutes. The reaction mixture was concentrated to dryness and the solids were washed with methylene chloride, dried over magnesium sulfate and concentrated to give 3-[4-(4-Chloro-phenyl)-3,6-dihydro-2H-pyridin-1-yl]-propylamine (0.82 g, 64%) as a waxy white solid. Mp. 57–58° C.; NMR CDCl$_3$ δ 7.29–7.20 (m, 4H), 6.03 (s, 1H), 3.12 (d, J=3.3 Hz, 2H), 2.76 (t, J=6.9 Hz, 2H), 2.67 (t, J=5.6 Hz, 2H), 2.51–2.44 (m, 4H), 1.69 (p, J=7.5 Hz, 2H), 1.63 (s, 2H); $^{13}$C NMR CDCl$_3$ δ 139.20, 133.96, 132.61, 128.36, 126.15, 122.41, 56.20, 53.36, 50.30, 40.77, 30.73, 28.01; IR(KBr) 2929, 2861, 2805, 2767, 2734, 1493, 1467, 1379, 1320, 1128, 1095, 845, 825, 800; Analysis calculated for $C_{14}H_{19}ClN_2 \cdot 0.25H_2O$: C, 65.87; H, 7.70; N, 10.97. Found: C, 65.69; H, 7.44; N, 10.91.

Example 5

Preparation of 3-[2,4-Dioxo-1,4-dihydro-2H-quinazolin-3-yl]propionaldehyde

Benzoylene urea (4.0 g, 24.7 mmol), Triton B (40 wt % in methanol) (11.0 mL, 24.7 mmol), water (80 mL) and methanol (400 mL) were combined at ambient temperature and stirred vigorously for 15 minutes. (until all the solids had gone into solution). To this colorless solution, acrolein (1.7 mL, 24.7 mmol) in methanol (20 mL) was added dropwise over 5 minutes. to give a yellow solution. The reaction was then heated to 55 ° C. and stirred for 2 hours. and then at room temperature for approximately 16 hours. The yellow solution was concentrated to give a yellow oil which was taken up in ethyl acetate (25 mL) and water (50 mL). The aqueous layer was extracted again with ethyl acetate (25 mL). The organic layers were combined, washed with IN HCl (20 mL), water (20 mL), saturated sodium bicarbonate solution (20 mL) and brine (20 mL), the organic layer was dried over magnesium sulfate and concentrated to give 3-[2,4-dioxo-1,4-dihydro-2H-quinazolin-3-yl] propionaldehyde as a yellow foam (3.2 g, 59%) which was used without further purification. The NMR data showed a purity of 70%. NMR CDCl$_3$ δ 9.85 (s, 1H), 8.10–8.06 (m, 1H), 7.63–7.57 (m, 1H), 7.24–7.19 (m, 1H), 7.13–7.07 (m, 1H), 4.44–4.40 (m, 2H), 2.85 (dt, 2H, J$_{1,2}$=2 Hz, J$_{1,3}$=7 Hz); MS=219 (p+1).

Example 6

Preparation of 3-{3-[4-(3,5-dichloro-pyridin-2 yl)-piperazin-1-yl]propyl}-1H-quinazoline-2,4-dione 3-[2,4-Dioxo-1,4-dihydro-2H-quinazolin-3-yl] propionaldehyde (0.19 g, 0.69 mmol), 1-(3,5-dichloro-pyridin-2-yl)-piperazine (0.19 g, 0.83 mmol), sodium triacetoxyborohydride (0.18 g, 0.83 mmol) and dichloroethane (15 mL) were combined at ambient temperature and stirred overnight for 16 hours. The reaction was diluted with 10% sodium bicarbonate solution (20 mL) and stirred for 30 minutes. The organic phase was collected, washed with brine (20 mL), dried over magnesium sulfate, and concentrated to yield a yellow oil (0.291 g). The crude product was chromatographed using 16 g silica gel and ethyl acetate as the eluent, yielding 3-{3-[4-(3,5-dichloro-pyridin-2-yl)-piperazin-1yl-]-propyl}-1H-quinazoline-2,4-dione (0.076 g, 26%) as a colorless oil. NMR CDCl$_3$ δ 10.68 (s, 1H), 8.09–8.05 (m, 2H), 7.58 (t,1H, J=8 Hz), 7.54–7.52 (m, 1H), 7.19 (t, 1H, J=8 Hz), 7.11 (d, 1H, 4.15 (t, 2H, J=7 Hz), 3.31 (bs, 4H), 2.61–2.54 (m, 6H), 2.01–1.92 (m, 2H); MS=435 (p+1).

Example 7

Preparation of 11, 3-{3-[4-(4-Chloro-phenyl)-3,6-dihydro-2H-pyridinyl-1-yl]-propyl}-6-methyl-1H-quinazoline-2,4-dione 2-Amino-5-methylbenzoic acid, methyl ester (0.250 g, 1.51 mmol) and triethylamine (0.48 mL, 3.47 mmol) in methylene chloride (8 mL) were cooled in an ice bath. Triphosgene (0.149 g, 0.503 mmol) was added and the resulting mixture was stirred for 1 h at 0° C. to form the isocyanate intermediate. 3-[4-(4-Chloro-phenyl)-3,6-dihydro-2H-pyridin-1-]-propylamine (0.379 g, 1.51 mmol) was added in one portion and the mixture was stirred for 15 h at room temperature. The mixture was concentrated, added toluene (30 mL) and refluxed for 24 h. The mixture was diluted with sat. sodium bicarbonate and extracted with 3 times ethyl acetate (200 mL). Pooled ethyl acetate was washed with brine (200 mL), dried over magnesium sulfate and concentrated to give a white solid. Flash chromatography using 5% methanol/chloroform as eluent gave 3-{3-[4-(4-Chloro-phenyl)-3,6-dihydro-2H-pyridinyl-1-yl]-propyl}-6-1H-quinazoline-2,4-dione (0.49 g, 79%) as a white solid. The maleate salt had the following properties: M.p. 199–201° C.; $^1$H NMR DMSO-d$_6$ δ 11.39 (s, 1H), 9.45 (brd s, 1H), 7.71 (s,1H), 7.45 (dd, J=8.1, 22.0 Hz, 4H), 7.07 (d, J=9.5 Hz, 1H), 6.20 (brd s, 1H), 5.99 (s, 2H), 3.96 (t, J=6.9 Hz, 2H), 3.82–3.60 (m, 2H), 3.40–3.00 (m, 2H), 2.69 (brd s, 2H), 2.30 (s, 2H), 2.08–1.95 (m, 2H); $^{13}$C NMR DMSO-d$_6$ δ 167.64, 162.67, 150.70, 137.78, 137.46, 136.59, 136.01, 133.45, 133.01, 132.22,. 129.15, 128.88, 127.22, 127.06, 126.97, 115.68, 115.43, 114.10, 53.44, 37.83, 26.48, 23.27, 20.66; IR (KBr) 3052, 2959, 2300, 1719, 1659, 1629, 1578, 1516, 1459, 1374, 1354, 1283, 1196, 1097, 1072, 1011, 984, 957, 946, 883, 873, 827, 811, 800, 776, 729, 720, 699, 678, 648, 625, 584, 556, 546, 530, 464, 431, 406; Analysis calculated for C$_{23}$H$_{24}$ClN$_3$O$_2$.C$_4$H$_4$O$_4$: C, 61.66; H, 5.37; N, 7.99. Found: C, 61.64; H, 5.57; N, 7.98.

Example 8

Preparation of 3-{3-[4-(4-Chloro-phenyl)-3,6-dihydro-2H-pyridinyl-1-yl]-propyl}-8-methoxy-1H-quinazoline-2,4-dione The same general procedure was followed as in Example 7 with starting materials, 2-amino-3-methoxy-benzoic acid, methyl ester and 3-[4-(4-Chloro-phenyl)3,6-dihyro-2H-pyridin-1yl]-propylamine to yield 3-{3-[4-(4-Chloro-phenyl)-3,6-dihydro-2H-pyridinyl-1-yl]-propyl}-8-methoxy-1H-quinazoline-2,4-dione. The maleate salt of the compound has the following was found to have: Mp. 195–197° C.; $^1$H NMR DMSO-d$_6$ δ 10.90 (s, 1H), 9.45 (brd s, 1H), 7.65–7.38 (m, 5H), 7.29 (d, J=8.1 Hz, 1H), 7.14 (t, J=8.1 Hz, 1H), 6.20 (brd s, 1H), 5.99 (s, 2H), 4.02–3.94 (m, 2H), 3.86 (s, 3H), 3.83–3.69 (m, 2H), 3.37–3.26 (m, 2H), 3.24–3.07 (m, 2H), 2.75–2.64 (m, 2H), 2.08–1.98 (m, 2H); $^{13}$C NMR DMSO-d$_6$ δ 167.65, 162.54, 150.51, 146.58, 137.45, 136.55, 136.05, 133.45, 133.01, 130.21, 129.15, 128.88, 127.24, 126.97, 123.06, 122.83, 118.88, 114.90, 56.71, 53.45, 37.93, 24.33, 23.18;IR (KBr) 3192,3072, 2968, 2939, 2846, 2426, 1907, 1714, 1661, 1621, 1515, 1491, 1450, 1432, 1415, 1389, 1356, 1321, 1269, 1210, 1084, 1047, 1012, 997, 978, 943, 915, 871, 844, 810, 782, 754, 729, 694, 665, 647, 590, 537, 522, 513, 463, 420, 412; Analysis calculated for C$_{23}$H$_{24}$ClN$_3$O$_3$.C$_4$H$_4$O$_4$: C, 59.84; H, 5.21; N, 7.75. Found: C, 59.60; H, 5.27; N, 7.64.

Example 9

Preparation of 3-{3-[4-(4-Chloro-phenyl)-3,6-dihydro-2H-pyridinyl-1-yl]-propyl}-8-chloro-1H-quinazoline-2,4dione The same general procedure was followed as in Example 7 with starting materials, 2-amino-3-chloro-benzoic acid, methyl ester and 3-[4-(4-Chloro-phenyl)-3,6-dihydro-2H-pyridinyl-1-yl]-propyl}-8-chloro-1H-quinazoline-2,4-dione. The maleate salt of the compound has the following was found to have: Mp. 200–203° C.; $^1$H NMR DMSO-d$_6$ δ 11.06 (brd s, 1H), 7.91 (dd, J=1.2, 7.0 Hz, 1H), 7.79 (dd, J=1.3, 6.6 Hz, 1H), 7.74 (dd, J=8.5, 21.0 Hz, 4H), 7.2 9t, J=7.9 Hz, 1H), 6.2 (brd s, 1H), 5.98, (s,2H), 3.98 (t, J=6 Hz, 2H), 3.85–3.50 (m, 2H), 3.3 (m, 2H), 3.19 (m, 2H), 2.70 (m, 2H), 2.0 (m, 2H); $^{13}$C NMR DMSO-d$_6$ δ 167.59, 161.96, 150.52, 137.50, 136.87, 136.31, 135.45, 133.45, 132.99, 129.00, 127.10, 127.04, 123.61, 119.10, 116.42, 53.48, 50.41, 48.86, 38.22, 24.37, 23.09; IR (KBr) 3356, 3155, 3075, 2966, 2923, 2844, 2298, 1717, 1650, 1615, 1575, 1503, 1475, 1436, 1411, 1386, 1360, 1317, 1297, 1272, 1219, 1169, 1138, 1097, 1069, 1012, 984, 946, 873, 841, 804, 760, 732, 717, 666, 647, 588, 555, 535, 494, 452, 420, 407; Analysis calculated for C$_{22}$H$_{21}$Cl$_2$N$_3$O$_2$.C$_4$H$_4$O$_4$: C, 57.15; H, 4.61; N, 7.69. Found: C, 56.80; H, 4.63; N, 7.66.

Example 10

Preparation of 3-{3-[4-(4-Chloro-phenyl)-3,6-dihydro-2H-pyridin-1-yl]-propyl}-5-fluoro-1H-quinazoline-2,4-dione The same general procedure was followed as in Example 7 with starting materials, 2-amino-6-fluoro-benzoic acid, methyl ester and 3-[4-(4-Chloro-phenyl)3,6-dihyro-2H-pyridin-1yl]-propylamine to yield 3-{3-[4-(4-Chloro-phenyl)-3,6 dihydro-2H-pyridin-1-yl]-propyl}-5-fluoro-1-quinazoline-2,4-dione. The maleate salt of the compound has the following was found to have: Mp. 201–202° C.; $^1$H NMR DMSO-d$_6$ δ 7.71–7.64 (m, 1H), 7.54 (d, J=8.7 Hz, 2H), 7.46 (d, J=8.6 Hz, 2H), 7.04–6.97 (m, 2H), 6.26 (s, 1H), 6.05 (s, 2H), 4.00–3.00 (brd m, 8H), 2.76 (brd s, 2H), 2.10–2.00 (m, 2H); $^{13}$C NMR DMSO-d$_6$ δ 167.54, 150.50, 141.71, 137.42, 135.98, 133.46, 133.03, 129.02, 127.11, 111.60, 109.93, 53.38, 50.27, 48.82, 37.59, 24.27, 23.02; IR (KBr) 3273, 3223, 3024, 2968, 1715, 1660, 1631, 1454, 1354, 1080, 807 Analysis calculated for $C_{22}H_{21}Cl_2N_3O_2$.$C_4H_4O_4$.0.5H$_2$O: C, 57.94; H, 4.86; N, 7.80. Found: C, 57.57; H, 4.43; N, 7.69.

Example 11

Preparation of 3-{3-[4-(4-Chloro-phenyl)-3,6-dihydro-2H-pyridin-1-yl]-propyl}-6-fluoro-1H-quinazoline-2,4-dione The same general procedure was followed as in Example 7 with starting materials, 2-amino-5-fluoro-benzoic acid, methyl ester and 3-[4-(4-Chloro-phenyl)-3,6-dihydro-2H-pyridin-1-yl]-propylamine to yield 3-{3-[4-(4-chloro-phenyl)-3,6dihydro-2H-pyridin-1-yl]-propyl}-6-fluoro-1-quinazoline-2,4-dione. The maleate salt of the compound has the following was found to have: Mp. 192–193° C.; $^1$H NMR DMSO-d$_6$ δ 7.69–7.58 (m, 2H), 7.54 (d, J=8.7 Hz, 2H), 7.46 (d, J=8.7 Hz, 2H), 7.27 (dd, J=4.5 Hz, 8.9 Hz, 2H), 6.26 (brd s, 1H), 6.04 (s,2H), 4.01 (t, J=6.4 Hz, 2H), 3.88 (br s, 2H), 3.36 (brd s, 1H), 3.24 (brd s, 2H),2.74 (brd s, 2H), 2.54–2.49 (m, 2H); $^{13}$C NMR DMSO-d$_6$ δ 167.58, 162.01, 159.55, 150.48, 137.47, 136.66, 136.25, 133.44, 133.00, 129.00, 127.10, 123.65, 123.42, 117.97, 115.37, 112.73, 112.63, 53.44, 50.37, 48.85, 38.04, 24.37, 23.15; IR (KBr) 3083, 29.64, 22.90, 1716. 1666, 1619, 1572, 1462, 1361, 1098, 1072, 871, 829, 775, 674, 557; Analysis calculated for $C_{22}H_{21}Cl_2N_3O_2$.$C_4H_4O_4$.0.5H$_2$O: C, 57.94; H, 4.86; N, 7.80. Found C, 57.70; H, 4.65; N, 7.73.

Example 12

Preparation of 3-{3-[4-(4-Chloro-phenyl)-3,6-dihydro-2H-pyridin-1-yl]-propyl}7-fluoro-1H-quinazoline-2,4-dione The same general procedure was followed as in Example 7 with starting materials, 2-amino-4-fluoro-benzoic acid, methyl ester and 3-[4-(4-Chloro-phenyl)3,6-dihyro-2H-pyridin-1-yl]-propylamine to yield 3-{3-[4-(4-Chloro-phenyl)-3,6-dihydro-2H-pyridin-1-yl]-propyl}-7-fluoro-1H-quinazoline-2,4-dione. The maleate salt of the compound has the following was found to have: Mp. 197–198° C.; $^1$H NMR DMSO-d$_6$ δ 8.03 (dd, J=6.2, 8.7 Hz, 1H), 7.54 (d, J=8.7 Hz, 2H), 7.46 (d, J=8.7 Hz, 2H), 7.09 (dt, J=2.5, 8.7 Hz, 1H), 6.95 (dd, J=2.5, 9.9, 1H), 6.25 (brd s, 1H), 6.04 (s, 2H), 4.00 (t, J=6.4 Hz, 2H), 3.86 (brd s, 2H), 3.36 (brd s, 2H), 3.24 (brd, s, 2H) 2.75 (brd s, 2H), 2.10–2.04 (m, 2H); $^{13}$C NMR DMSO-d$_6$ δ 167.58, 162.60, 161.86, 150.74, 141.85, 137.47, 136.25, 133.45, 133.00, 131.12, 129.00, 127.10, 111.37, 111.18, 110.95, 101.85, 101.60, 53.42, 50.35, 48.85, 37.90, 24.39, 23.17; IR (KBr) 3004, 2911, 1726, 1665, 1626, 1579, 1494, 1397, 1372, 1356, 1286, 1179, 1101, 862, 767; Analysis calculated for $C_{22}H_{21}ClFN_3O_2$.$C_4H_4O_4$. 0.25 H$_2$O; C, 58.43; H, 4.81; N, 7.86; Found: C, 58.23; H, 4.46; N, 7.90.

Example 13

Preparation of 3-{3-[4-(4-Chloro-phenyl)-3,6-dihydro-2H-pyridin-1-yl]propyl}-6,7-difluoro-1-quinazoline-2,4-dione The same general procedure was followed as in Example 7 with starting materials, 2-amino-4,5-difluoro-benzoic acid, methyl ester and 3-[4-(4-Chloro-phenyl)-3,6-dihyro-2H-pyridin-1-yl]-propylamine to yield 3-{3-[4-(4-Chloro-phenyl)-3,6-dihydro-2H-pyridin-1-yl]-propyl}-6,7-difluoro-1H-quinazoline-2,4-dione. The maleate salt of the compound has the following was found to have: Mp. 204–205° C.; $^1$H NMR DMSO-d$_6$ δ 7.93 (dd, J=8.6, 10.2 Hz, 1H), 7.54 (d, J=8.7 Hz, 2H), 7.45 (d, J=8.7 Hz, 2H), 7.16 (dd, J=10.9, 6.6 Hz, 1H), 6.25 (brd s, 1H), 6.04 (s, 1H), 4.00 (t, J=6.4 Hz, 2H), 3.87 (brd s, 2H), 3.39 (brd s, 2H), 3.26–3.21 (m, 2H) 2.74 (brd s, 2H), 2.10–2.04 (m, 2H); $^{13}$C NMR DMSO-d$_6$ δ 167.59, 161.35, 150.53, 137.46, 136.19, 133.45, 132.98, 129.00, 127.08, 117.94, 116.10, 115.91, 110.00, 104.48, 104.26, 53.38, 50.35, 48.83, 38.09, 24.36, 23.08; IR (KBr) 3079, 3012, 2961, 1723, 1663, 1626, 1575, 1516, 1458, 1396, 1357, 1302, 1092, 864, 779, 769; Analysis calculated for $C_{22}H_{20}ClFN_3O_2$. $C_4H_4O_4$; C, 56.99; H, 4.41; N, 7.67; Found: C, 56.76; H, 4.23; N, 7.91.

Example 14

Preparation of 5-Chloro-3-{3-[4-(4-chloro-phenyl)-3,6-dihydro-2H-pyridin-1-yl]propyl}-1H-quinazoline-2,4-dione The same general procedure was followed as in Example 7 with starting materials, 2-amino-6-chloro-benzoic acid, methyl ester and 3-[4-(4-Chloro-phenyl)-3,6-dihydro-2H-pyridin-1-yl]propylamine to yield 5-Chloro-3-{3-[4-(4-chloro-phenyl)-3,6-dihydro-2H-pyridin-1-yl[-propyl}-1H-quinazoline-2,4-dione. The maleate salt of the compound has the following was found to have: Mp. 190–194° C.; $^1$H NMR DMSO-d$_6$δ 11.60 (s, 2H), 9.44 (brd s, 1H), 7.56 (t, J=8 Hz, 1H), 7.45 (dd, J=9, 31 Hz, 4H), 7.22 (d, J=8 Hz, 1H), 7.13 (d, J=8 Hz, 1H), 6.21 (bs, 1H), 5.99 (s, 1H), 3.95–3.92 (m, 2H), 3.84–3.49 (m, 2H), 3.35–3.14 (m, 4H), 2.77–2.6 (m, 2H), 2.10–1.95 (m, 2H); IR (KBr) 3668, 3375, 3128, 3058, 2970, 2919, 2879, 2837, 2767, 2740, 2116, 1953, 1863, 1713, 1674, 1608, 1589, 1554, 1491, 1452, 1396, 1380, 1366, 1330, 1318, 1299, 1265, 1241, 1222, 1205, 1196, 1166, 1152, 1118, 1094, 1074, 1047, 1011, 1000, 971, 948, 896, 843, 833, 821, 805, 798, 767, 752, 727, 683, 633, 608, 588, 561, 536, 515, 488, 474, 463, 428, 405; Analysis calculated for $C_{22}H_{21}Cl_2N_3O_2$.$C_4H_4O_4$; C, 57.15; H, 4.61; N, 7.69; Found: C, 57.02; H, 4.62; N, 7.67.

Example 15

Preparation of 6-Chloro-3-{3-[4-(4-chloro-phenyl)-3,6-dihydro-2H-pyridin-1-yl]propyl}-1H-quinazoline-2,4-dione The same general procedure was followed as in Example 7 with starting materials, 2-amino-5-chloro-benzoic acid, methyl ester and 3-[4-(4-Chloro-phenyl)-3,6-dihyro-2H-pyridin-1-yl]-propylamine to yield 6-Chloro-3-{3-[4-(4-chloro-phenyl)-3,6-dihydro-2H-pyridin-1-yl]-propyl}-1H-quinazoline-2,4-dione. The tmaleate salt of the compound has the following was found to have: Mp. 197–198° C.; $^1$H NMR DMSO-d$_6$ δ 11.62 (s, 1H), 7.84 (d, J=2.3 Hz, 1H), 7.69 (dd, J=8.7, 2.3 Hz, 1H), 7.47 (d, J=8.5 Hz, 2H), 7.40 (d, J=8.5 Hz, 2H), 7.18 (d, J=8.7 Hz, 1H), 6.20 (s, 1H), 5.99 (s, 2H), 3.97 (t, J=8.0 Hz, 2H), 3.45–3.10 (m, 6H), 2.69 (brd s, 2H), 2.10–1.97 (m, 2H); $^{13}$C NMR DMSO-d$_6$ δ 167.59, 161.75, 150.49, 138.79, 137.45, 136.23, 135.37, 133.43, 133.00, 129.01, 127.09, 126.89, 126.70, 117.84, 115.74, 53.37, 50.32, 48.83, 38.04, 24.29, 23.11, 20.99; IR (KBr) 3073, 2969, 2934, 2313, 1728, 1651, 1620, 1489, 1454, 1357, 1275, 1214, 1090, 868, 821, 675, 528; $C_{22}H_{21}Cl_2N_3O_2$.$C_4H_4O_4$; C, 57.15; H, 4.61; N, 7.69; Found: C, 57.08; H, 4.60; N, 7.60.

Example 16

Preparation of 7-Chloro-3-{3-[4-(4-chloro-phenyl)-3,6-dihydro-2H-pyridin-1-yl]propyl}-1H-quinazoline-2,4-dione The same general procedure was followed as in Example 7 with starting materials, 2-amino-4-chloro-benzoic acid, methyl ester and 3-[4-(4-Chloro-phenyl)-3,6-dihyro-2H-pyridin-1-yl]-propylamine to yield 7-Chloro-3-{3-[4-(4-chloro-phenyl)-3,6-dihydro-2H-pyridin-1-yl]-propyl}-1H-quinazoline-2,4-dione. The maleate salt of the compound has the following was found to have: Mp. 225–227° C.; $^1$H NMR DMSO-d$_6$ δ 11.59 (s, 1H), 9.50 (brd s, 1H), 7.92 (d, J=8.5 Hz, 1H), 7.45 (dd, J=8.5, 20.8 Hz, 4H), 7.24 (dd, J=1.9, 6.6 Hz, 1H), 7.17–7.20 (m, 1H), 6.20 (brd s, 1H), 5.99 (s, 2H), 3.95 (t, J=6.4 Hz, 2H) 3.50–3.80 (m, 2H), 3.08–3.3 (m, 4H), 2.69 (brd s, 2H), 2.01 (m, 2H); IR (KBr) 3189, 3067, 2978, 2884, 2742, 2609, 1717, 1662, 1616, 1598, 1445, 1430, 1355, 1296, 1267, 1254, 1208, 1176, 1085, 1055, 1011, 943, 922, 906, 864, 839, 811, 787, 769, 736, 698, 686, 681, 647, 581, 524, 467, 444, 411; Analysis calculated for $C_{22}H_{21}Cl_2N_3O_2.C_4H_4O_4$: C, 57.15; H, 4.61; N, 7.69. Found: C, 57.31; H, 4.75; N, 7.68.

Example 17

Preparation of 5,8-Dichloro-3-{3-[4-(4-chloro-phenyl)-3,6-dihydro-2H-pyridin-1-yl]-propyl}-1H-quinazoline-2,4-dione The same general procedure was followed as in Example 7 with starting materials, 2-amino-3,6-dichloro-benzoic acid, methyl ester and 3-[4-(4-Chloro-phenyl)-3,6-dihydro-2H-pyridin-1-yl]-propylamine to yield 5,8-Dichloro-3-{3-[4-(4-chloro-phenyl)-3,6-dihydro-2H-pyridin-1-yl]-propyl}-1H-quinazoline-2,4-dione. The maleate salt of the compound has the following was found to have: M.p. 207–209° C.; $^1$H NMR DMSO-d$_6$ δ 10.94 (brd s, 1H), 9.53 (brd s, 1H), 7.74 (d, J=10 Hz, 1H), 7.44 (dd, J=8.5, 22.4 Hz, 4H), 7.25 (d, J=8.5 Hz, 1H), 6.21 (s, 1H), 5.99 (s, 2H), 4.05–3.90 (m, 2H), 3.89–3.69 (m, 2H), 3.58–3.26 (m, 2H), 3.25–3.09 (m, 2H), 2.76–2.62 (m, 2H), 2.10–1.97 (m, 2H); IR (KBr) 3380, 3203, 3116, 3073, 3007, 2974, 2740, 2597, 1877, 1723, 1672, 1592, 1496, 1408, 1394, 1367, 1346, 1314, 1298, 1280, 1261, 1249, 1233, 1194, 1173, 1152, 1127, 1094, 1074, 1009, 965, 925, 894, 864, 830, 804, 757, 737, 664, 598, 587, 572, 526, 510, 480, 464, 452, 419; Analysis calculated for $C_{22}H_{20}C_3N_3O_2.C_4H_4O_4$: C, 53.76; H, 4.16; N, 7.23. Found: C, 53.72; H, 4.07; N, 7.15.

Example 18

Preparation of 6,8-Dichloro-3-{3-[4-(4-chloro-phenyl)-3,6-dihydro-2H-pyridin-1-yl]-propyl}-1H-quinazoline-2,4-dione The same general procedure was followed as in Example 7 with starting materials, 2-amino-3,5-dichloro-benzoic acid, methyl ester and 3-[4-(4-Chloro-phenyl)-3,6-dihyro-2H-pyridin-1-yl]-propylamine to yield 6,8-Dichloro-3-{3-[4-(4-chloro-phenyl)-3,6-dihydro-2H-pyridin-1-ly]-propyl}-1H-quinazoline-2,4-dione. The maleate salt of the compound has the following was found to have: M.p. 197–199° C.; $^1$H NMR DMSO-d$_6$ δ 11.23 (brd s, 1H), 9.60 (brd s, 1H), 7.95 (d, J=2.5 Hz, 1H), 7.85 (d, J=2.3 Hz, 1H), 7.44 (dd, J=8.7, 21.0 Hz, 4H), 6.20 (brd s, 1H), 5.99 (s, 2H), 3.97 (t, J=6.2 Hz, 2H), 3.89–3.69 (m, 2H), 3.40–3.26 (m, 2H), 3.26–3.08 (m, 2H), 2.75–2.69 (m, 2H), 2.03–1.95 (m, 2H); IR (KBr) 3152, 3116, 3071, 2970, 2833, 2276, 1717, 1649, 1612, 1498, 1463, 1354, 1316, 1273, 1216, 1172, 1154, 1116, 1083, 1013, 985, 942, 908, 894, 872, 826, 807, 777, 724, 704, 654, 615, 591, 569, 533, 479, 450, 415; Analysis calculated for $C_{22}H_{20}Cl_3N_3O_2.C_4H_4O_4$: C, 53.76; H, 4.17; N, 7.23. Found: C, 53.68; H, 4.06; N, 7.21.

Example 19

Preparation of 3-{3-[4-(4-Chloro-phenyl)-3,6-dihydro-2H-pyridin-1-yl]-propyl}-5-methyl-1H-quinazoline-2,4-dione The same general procedure was followed as in Example 7 with starting materials, 2-amino-6-methyl-benzoic acid, methyl ester and 3-[4-(4-Chloro-phenyl)-3,6-dihydro-2H-pyridin-1-yl]-propylamine to yield 3-{3-[4-(4-Chloro-phenyl)-3,6-dihydro-2H-pyridin-1-yl]-propyl}-5-methyl-1H-quinazoline-2,4-dione. The maleate salt of the compound has the following was found to have: mp=175–178° C.; $^1$H NMR DMSO-d$_6$ δ 11.35 (bs, 1H), 7,51–7.38 (m, 5H), 6.99 (dd, J=8, 18 Hz), 6.21(s, 1H), 5.99 (s, 2H), 3.94 (t, J=7 Hz, 2H), 3.85–3.54 (m, 2H), 3.26–3.12 (m, 2H), 2.24–2.67 (m, 2H), 2.66 (s, 3H), 2.06–1.95 (m, 2H); IR (KBr) 3183, 3089, 3027, 2953, 2613, 1949, 1716, 1654, 1614, 1598, 1521, 1496, 1477, 1451, 1407, 1382, 1362, 1305, 1281, 1250, 1194, 1148, 1100, 1076, 1058, 1012, 984, 940, 878, 860, 829, 796, 785, 735, 696, 683, 665, 617, 597, 578, 537, 475, 440, 415; Analysis calculated for $C_{23}H_{24}ClN_3O_2.C_4H_4O_4$; C, 61.65; H, 5.37; N, 7.99; Found: C, 61.44; H, 5.21; N, 7.97.

Example 20

Preparation of 3-{3-[4-(4-Chloro-phenyl)-3,6-dihydro-2H-pyridin-1-yl]-propyl}-7-methyl-1H-quinazoline-2,4-dione The same general procedure was followed as in Example 7 with starting materials, 2-amino-4-methyl-benzoic acid, methyl ester and 3-[4-(4-Chloro-phenyl)-3,6-dihyro-2H-pyridin-1-yl]-propylamine to yield 3-{3-[4-(4-Chloro-phenyl)-3,6-dihydro-2H-pyridin-1-yl]-propyl}-7-methyl-1H-quinazoline-2,4-dione. The maleate salt of the compound has the following was found to have: Mp. 199–201° C.; $^1$H NMR DMSO-d$_6$ δ 10.75 (s, 1H), 9.46 (brd s, 1H), 7.80 (d, J=8.1 Hz, 1H), 7.45 (dd J=7.1, 23.5 Hz, 5H) 7.10 (t, J=7.5 Hz, 1H), 6.20 (brd s, 1H), 5.99 (s, 2H), 3.99 (t, J=6.2 Hz, 2H), 3.86–3.55 (m, 2H), 3.36–3.27 (m, 2H), 3.28–3.11 (m, 2H), 2.73–2.62 (m, 2H), 2.33 (s, 3H), 2.09–1.98 (m, 2H); IR (KBr) 3226, 3191, 3150, 3074, 2958, 2302, 1716, 1648, 1609, 1575, 1462, 1437, 1388, 1358, 1330, 1296, 1273, 1220, 1201, 1096, 1075, 1012, 983, 947, 916, 874, 804, 765, 733, 717, 708, 670, 647, 589, 532, 484, 465, 429, 415, 409; Analysis calculated for $C_{23}H_{24}ClN_3O_2.C_4H_4O_4$: C, 61.66; H, 5.37; N, 7.99. Found: C, 61.92; H, 5.46; N, 8.23.

Example 21

Preparation of 3-{3-[4-(4-Chloro-phenyl)-3,6-dihydro-2H-pyridin-1-yl]-propyl}-8-methyl-1H-quinazoline-2,4-dione The same general procedure was followed as in Example 7 with starting materials, 2-amino-3-methyl-benzoic acid, methyl ester and 3-[4-(4-Chloro-phenyl)-3,6-dihyro-2H-pyridin-1-yl]-propylamine to yield 3-{3-[4-(4-Chloro-phenyl)-3,6-dihydro-2H-pyridin-1-yl]-propyl}-8-methyl- 1H-quinsxolinr-2,4-dione. The maleate salt of the compound has the following was found to have: Mp. 215–217° C.; $^1$H NMR CDCl$_3$ δ 13.17 (s, 1H), 9.05 (brd s, 1H), 7.94 (d, J=7.3 Hz, 1H), 7.46 (d, J=7.3 Hz, 1H), 7.24–7.31 (m, 4H), 7.12 (t, J=7.7 Hz, 1H), 5.99 (s, 2H), 5.95 (brd s, 2H), 4.20 (t, 5.8 Hz, 2H), 3.55–3.80 (m, 2H), 3.37–3.24 (m, 2H), 3.10–2.90 (m, 2H), 2.61–2.49 (m, 2H), 2.40 (s, 3H), 2.33–2.21 (m, 2H); IR (KBr) 3192, 3070, 2959, 1715, 1648, 1609, 1576, 1462, 1437, 1388, 1357, 1330, 1272, 1200, 1096, 1076, 1012, 983, 947, 873, 805, 764, 733, 647, 588, 533, 465; Analysis calculated for $C_{23}H_{24}ClN_3O_2 \cdot C_4H_4O_4 \cdot 1/3$ H$_2$O: C, 60.96; H, 5.43; N, 7.90. Found: C, 61.02; H, 5.48; N, 7.89.

Example 22

Preparation of 3-{3-[4-(4-Chloro-phenyl)-3,6-dihydro-2H-pyridin-1-yl]-propyl}-5,8-dione The same general procedure was followed as in Example 7 with starting materials, 2-amino-3,6-dimethyl-benzoic acid, methyl ester and 3-[4-(4-Chloro-phenyl)-3,6-dihydro-2H-pyridin-1-yl]-propylamine to yield 3-{3-[4-(4-Chloro-phenyl)-3,6-dihydro-2H-pyridin-1-yl]-propyl}-5,8-dimethyl-1H-quinazoline-2,4-dione. The maleate salt of the compound has the following was found to have: Mp. 212–220° C.; $^1$H NMR CDCl$_3$ δ 8.19 (brd s, 1H), 7.33–7.26 (m, 5H), 6.90 (d, J=8 Hz, 1H), 6.02 (s, 2H), 5.98–5.93 (m, 1H), 4.14 (t, J=6 Hz, 2H), 3.84–2.85 (m, 8H), 2.70 (s, 3H), 2.34 (s, 3H), 2.31–2.19 (m, 2H); IR (KBr) 3342, 3232, 3199, 3106, 2974, 2924, 2864, 2734, 2354, 1709, 1658, 1641, 1592, 1467, 1410, 1377, 1354, 1309, 1269, 1258, 1240, 1190, 1162, 1093, 1069, 1035, 1010, 978, 954, 881, 861, 808, 777, 725, 710, 677, 649, 584, 565, 537, 511, 497, 486, 468, 433, 418; Analysis calculated for $C_{24}H_{26}ClN_3O_2 \cdot C_4H_4O_4$; C, 62.28; H, 5.60; N, 7.78; Found: C, 61.38; H, 5.53; N, 7.72.

Example 23

Preparation of 3-(3-[4-(4-Chloro-phenyl)-3,6-dihydro-2H-pyridin-1-yl]propyl}-6,8-dimethyl-1-quinazoline-2,4-dione The same general procedure was followed as in Example 7 with starting materials, 2-amino-3,5-dimethyl-benzoic acid, methyl ester and 3-[4-(4-Chloro-phenyl)-3,6-dihydro-2H-pyridin-1-yl]-propylamine to yield 3-{-3-[4-(4-Chloro-phenyl)-3,6-dihydro-2H-pyridin-1-yl]-propyl}-6,8-dimethyl-1Hquinazoline-2,4-dione. The maleate salt of the compound has the following was found to have: Mp. 224–226° C.; $^1$H NMR DMSO-d$_6$ δ 10.68 (s, 1H), 9.44 (brd s, 1H), 7.69 (s, 1H), 7.44 (dd, J=8.7, 21.4 Hz, 4H) 7.32 (s, 1H), 6.20 (brd s, 1H), 5.99 (s, 2H), 3.98 (t, J=6.2 Hz, 2H), 3.84–3.51 (m, 2H), 3.37–3.24 (m, 2H), 3.25–3.10 (m, 2H), 2.74–2.62 (m, 2H), 2.29 (s, 3H), 2.27 (s, 3H), 2.08–1.97 (m, 2H); IR (KBr) 3345, 3184, 3146, 3064, 2967, 2291, 1823, 1713, 1642, 1573, 1483, 1382, 1354, 1323, 1271, 1206, 1163, 1089, 1013, 983, 944, 915, 872, 841, 808, 783, 762, 726, 711, 652, 632, 589, 569, 549, 531, 485, 450; Analysis calculated for $C_{24}H_{26}ClN_3O_2 \cdot C_4H_4O_4$: C, 62.28; H, 5.60; N, 7.78. Found: C, 62.22; H, 5.44; N, 7.65.

Example 24

Preparation of 3-{3-[4-(4-Chloro-phenyl)-3,6-dihydro-2H-pyridin-1-yl]-propyl}-8-triflouromethyl-1H-quinazoline-2,4-dione The same general procedure was followed as in Example 7 with starting materials, 2-amino-3-trifluoromethyl-benzoic acid, methyl ester and 3-[4-(4-Chloro-phenyl)-3,6-dihydro-2H-pyridin-1-yl]-propylamine to yield 3-{3-[4-(4-Chloro-phenyl)-3,6-dihydro-2H-pyridin-1-yl]-propyl}-8-trifluoromethyl-1H-quinazoline-2,4-dione. The maleate salt of the compound has the following was found to have: Mp. 199 201° C.; $^1$H NMR CDCl$_3$ δ 13.17 (brd s, 1H), 8.32 (d, J=7.3 Hz, 1H), 8.21 (brd s, 1H), 7.90 (d, J=7.5 Hz, 1H), 738–7.23 (m, 5H), 6.14 (s, 2H), 5.97 (brd s, 1H), 4.16 (t, 6.4 Hz, 2H), 3.80–3.43 (m, 2H), 3.35–3.20 (m, 2H), 3.19–2.90 (m, 2H), 2.85–2.54 (m, 2H), 2.33–2.22 (m, 2H).

Example 25

Preparation of 3-{3-[4-(4-Chloro-phenyl)-3,6-dihydro-2H-pyridin-1-yl]-propyl}-8-hydroxy-1H-quinazoline-2,4-dione The same general procedure was followed as in Example 7 with starting materials, 2-amino-3-hydroxy-benzoic acid, methyl ester and 3-[4-(4-Chloro-phenyl)-3,6-dihydro-2H-pyridin-1-yl]-propylamine to yield 3-{3-[4-(4-Chloro-phenyl)-3,6-dihydro-2H-pyridin-1-yl]-propyl}-8-hydroxy-1H-quinazoline-2,4-dione. The hydrobromide salt of the compound has the following was found to have: Mp. 284–286° C.; $^1$H NMR DMSO-d$_6$ δ 10.66 (s, 1H), 10.42 (s, 1H), 9.47 (brd s, 1H), 7.46 (dd, J=8.7, 22.8 Hz, 4H), 7.37 (d, J=7.1 Hz, 1H), 7.12–6.97 (m, 2H), 6,21 (s, 1H),4.04–3.94 (m, 2H), 3.80–3.61 (m, 2H), 3.34–3.28 (m, 2H), 3.27–3.15 (m, 2H), 2.77–2.68 (m, 2H), 2.09–2.00 (m,2H); IR (KBr) 3199, 2955, 2929, 2815, 2691, 2656, 2591, 2412, 1940, 1877, 1711, 1662, 1625, 1608, 1516, 1495, 1432, 1416, 1384, 1364, 1269, 1191, 1149, 1097, 1068, 1037, 1012, 972, 942, 922, 879, 850, 831, 792, 761, 736, 716, 700, 667, 620, 589, 542, 512, 477, 457, 438, 414, 405; Analysis calculated for $C_{22}H_{22}ClN_3O_3 \cdot HBr$: C, 53.62; H, 4.70; N, 8.53. Found: C, 53.20; H, 4.77; N, 8.70.

Example 26

Preparation of 7-Chloro-3-{3-[4-(4-chloro-phenyl)-3,6-dihydro-2H-pyridin-1-yl]propyl}-8-methyl-1H-quinazoline-2,4-dione The same general procedure was followed as in Example 7 with starting materials, 2-amino-3-methyl-4-chloro-benzoic acid, methyl ester and 3-[4-(4-Chloro-phenyl)-3,6-dihyro-2H-pyridin-1-yl]-propylamine to yield 7-Chloro-3-{3-[4-(4-chloro-phenyl)-3,6-dihydro-2H-pyridin-1-yl]-propyl{-8-methyl-1H-quinazoline-2,4-dione. The maleate salt of the compound was found to have: Mp. 208–210° C.; $^1$H NMR DMSO-d$_6$ δ 10.90 (s, 1H), 9.44 (brd s, 1H), 7.80 (d, J=8.7 Hz, 1H), 7.46 (dd, J=8.7, 20.5 Hz, 4H) 7.28 (d, J=8.5 Hz, 1H), 6.20 (brd s, 1H), 6.00 (s, 2H), 3.98 (t, J=6.4 Hz, 2H), 3.84–3.54 (m, 2H), 3.38–3.26 (m, 2H), 3.25–3.10 (m, 2H), 2.75–2.624(m, 2H), 2.39 (s, 3H), 2.10–1.99 (m, 2H); IR (KBr) 3351, 3226, 3071 2965, 2728, 2603, 1904, 1714, 1656, 1612, 1596, 1448, 1353, 1321, 1294, 1261, 1205, 1152, 1134, 1094, 1011, 989, 950, 922, 866, 836, 811, 763, 729, 706, 682, 645, 579, 523, 511, 499, 468, 441, 404; Analysis calculated for $C_{23}H_{23}Cl_2N_3O_2 \cdot C_4H_4O_4$: C, 57.86; H, 4.86; N, 7.50. Found: C, 57.55; H, 4.79; N, 67.36.

Example 27

Preparation of 8-Bromo-3-{3-[4-(4-chloro-phenyl)-3,6-dihydro-2H-pyridin-1-yl]propyl}-6-methyl-1H-quinazoline-2,4-dione The same general procedure was followed as in Example 7 with starting materials, 2-amino-3-bromo-5- methylbenzoic acid, methyl ester and 3-[4-(4-Chloro-phenyl)-3,6-dihyro-2H-pyridin-1-yl]-propylamine to yield 8-Bromo-3-{3-[4-(4-chloro-phenyl)-3,6-dihydro-2H-pyridin-1-yl]-propyl}-6-methyl-1H-quinazoline-2,4-dione. The maleate salt of the compound has the following was found to have: Mp. 212–214° C.; $^1$H NMR DMSO-d$_6$ δ 10.60 (s, 1H), 9.45 (brd s, 1H), 7.79 (d, J=15.9 Hz, 1H), 7.46 (dd, J=8.7, 20.8 Hz, 4H), 6.20 (brd s, 1H), 5.99 (s, 2H), 3.98 (t, J=6.4 Hz, 2H), 3.84–3.51 (m, 2H), 3.38–3.26 (m, 2H), 3.25–3.04 (m, 2H), 2.75–2.63 (m, 2H), 2.31 (s, 3H), 2.09–1.97 (m, 2H); IR (KBr) 3160, 3109, 3064, 2969, 2281, 1715, 1646, 1622, 1573, 1510, 1478, 1447, 1378, 1352, 1323, 1272, 1196, 1082, 1013, 987, 947, 915, 870, 838, 806, 775, 725, 710, 646, 627, 588, 564, 540, 486, 448, 421; Analysis calculated for $C_{23}H_{23}BrClN_3O_2 \cdot C_4H_4O_4$: C, 53.61; H, 4.50; N, 6.95. Found: C, 53.60; H, 4.43; N, 6.88.

Example 28

Preparation of 3-{3-[4-(4-Chloro-phenyl)-3,6-dihydro-2H-pyridin-1-yl]propyl}-6-nitro-1H-quinazoline-2,4-dione The same general procedure was followed as in Example 7 with starting materials, 2-amino-5-nitro-benzoic acid, methyl ester and 3-[4-(4-Chloro-phenyl)-3,6-dihyro-2H-pyridin-1-yl]-propylamine to yield 3-{3-[4-(4-Chloro-phenyl)-3,6-dihydro-2H-pyridin-1-yl]-propyl}-6-nitro-1H-quinazoline-2,4-dione. The maleate salt of the compound has the following was found to have: Mp. 205–207° C.; $^1$H NMR DMSO-d$_6$ δ 12.10 (s, 1H), 9.43 (brd s, 1H), 8.62 (d, J=2.5 Hz, 1H), 8.47 (dd, J=2.3, 6.9 Hz, 1H), 7.45 (dd, J=8.3, 20.1 Hz, 4H) 7.33 (d, J=9.1 Hz, 1H), 6.21 (brd s, 1H), 6.00 (s, 2H), 3.98 (t, J=6.2 Hz, 2H), 3.84–3.45 (m, 2H), 3.38–3.06 (m, 4H), 2.75–2.61 (m, 2H), 2.10–1.95 (m, 2H); IR (KBr) 3194, 3084, 3045, 2941, 2420, 1722, 1674, 1612, 1576, 1550, 1490, 1456, 1375, 1356, 1316, 1295, 1240, 1207, 1169, 1116, 1086, 1012, 970, 954, 932, 884, 867, 848, 811, 792, 777, 757, 748, 725, 700, 689, 674, 650, 575, 550, 534, 514, 465, 450, 432; Analysis calculated for $C_{22}H_{21}ClN_4O_4 \cdot C_4H_4O_4$: C, 56.07; H, 4.52; N, 10.06. Found: C, 56.01; H, 4.58; N, 9.95.

Example 29

Preparation of 3-{3-[4-(4-Chloro-phenyl)-3,6-dihydro-2H-pyridin-1-yl]propyl}-7-nitro-1H-quinazoline-2,4-dione The same general procedure was followed as in Example 7 with starting materials, 2-amino-4-nitro-benzoic acid, methyl ester and 3-[4-(4-Chloro-phenyl)-3,6-dihyro-2H-pyridin-1-yl]-propylamine to yield 3-{3-[4-(4-Chloro-phenyl)-3,6-dihydro-2H-pyridin-1-yl}-7-nitro-1H-quinazoline-2,4-dione. The maleate salt of the compound has the following was found to have: Mp. 210–212° C.; $^1$H NMR DMSO-d$_6$ δ 11.85 (s, 1H), 9.47 (brd s, 1H), 8.16 (d, J=9.4 Hz, 1H), 7.97–7.92 (m, 1H), 7.45 (dd, J=8.5, 20.6 Hz, 4H), 6.20 (brd s, 1H), 5.99 (s, 2H), 3.98 (t, J=6.6 Hz, 2H), 3.87–3.49 (m, 2H), 3.35–3.07 (m, 4H), 2.78–2.61 (m, 2H), 2.08–1.97 (m, 2H); IR (KBr) 3196, 3069, 3052, 2956, 2926, 2816, 2770, 2730, 1718, 1665, 1625, 1537, 1491, 1449, 1396, 1380, 1345, 1314, 1278, 1258, 1248, 1238, 1202, 1184, 1163, 1142, 1127, 1092, 1066, 1051, 1043, 1012, 998, 963, 947, 933, 890, 844, 819, 799, 777, 745, 737, 726, 710, 701, 685, 678, 588, 558, 540, 524, 512, 500, 477, 459, 426, 412; $C_{22}H_{21}ClN_4O_4 \cdot C_4H_4O_4$: C, 56.07; H, 4.52; N, 10.06. Found: C, 55.90; H, 4.49; N, 9.95.

Example 30

Preparation of 5-Methyl-3-[3-(4-p-tolyl-3,6-dihydro-2H-pyridin-1-yl)-propyl]-1H-quinazoline-2,4-dione The same general procedure was followed as in Example 7 with starting materials, 2-amino-6-methyl-benzoic acid, methyl ester and 3-(4-p-tolyl-3,6-dihyro-2H-pyridin-1-yl)-propylamine to yield 5-methyl-3-[3-(4-p-tolyl-3,6-dihydro-2H-pyridin-1-yl)-propyl]-1H-quinazoline-2,4-dione. The maleate salt of the compound has the following was found to have: Mp. 165–170° C.; $^1$H NMR DMSO-d$_6$ δ 11.33 (brd s, 1H), 7.46 (t, J=8 Hz, 1H), 7.34 (d, J=8 Hz, 2H), 7.17 (d, J=8 Hz, 2H), 7.03 (d, J=8 Hz, 1H), 6.96 (d, J=8 Hz, 1H), 6.12 (brd s, 1H), 6.30 (s, 2H), 3.96 (t, J=7 Hz, 2H), 2.70 (s, 3H), 2.64–2.54 (m, 1H), 2.46–2.35 (m, 1H), 2.30 (s, 3H), 1.99–1.80 (m, 2H); IR (KBr) 3502, 3188, 3090, 3028, 2952, 2616, 1944, 1717, 1656, 1614, 1599, 1517, 1476, 1407, 1362, 1307, 1282, 1251, 1194, 1148, 1112, 1057, 1008, 941, 880, 861, 832, 796, 781, 760, 696, 682, 665, 617, 578, 537, 475, 441, 416, 401; Analysis calculated for $C_{24}H_{27}N_3O_2 \cdot C_4H_4O_4 \cdot 1H_2O$; C, 64.23; H, 6.35; N, 8.03. Found: C, 65.47; H, 5.92; N, 8.03.

Example 31

Preparation of 8-Chloro-3-{3-[4-(3-trifluoromethyl-phenyl)-3,6-dihydro-2H-pyridin-1-yl]-propyl}-1H-quinazoline-2,4-dione The same general procedure was followed as in Example 7 with starting materials, 2-amino-3-chloro-benzoic acid, methyl ester and 3-[4-(3-trifluoromethyl-phenyl)-3,6-dihyro-2H-pryidin-1-yl]-propylamine to yield 8-Chloro-3-{3-[4-(3-trifluoromethyl-phenyl)-3,6-dihydro-2H-pyridin-1-yl]-propyl}-1H-quinazoline-2,4-dione. The maleate salt of the compound has the following was found to have: Mp. 205–210° C.; $^1$H NMR DMSO-d$_6$ δ 11.10 (brd s, 1H), 7.97 (dd, J=2,8 Hz, 1H), 7.87–7.78 (m, 3H), 7.73–7.61 (m, 2H), 7.26 (t, J=8 Hz, 1H), 6.37 (brd s, 1H), 6.04 (s, 2H), 4.03 (t, J=7 Hz, 2H), 3.43–3.17 (m, 4H), 2.92–2.73 (m, 2H), 2.20–2.06 m, 2H), 1.68–1.40 (m, 2H); IR(KBr) 3220, 3152, 3071, 2968, 2922, 2249, 1809, 1715, 1646, 1614, 1579, 1504, 1478, 1438, 1411, 1389, 1356, 1330, 1272, 1251, 1171, 1122, 1080, 1021, 945, 906, 874, 830, 816, 794, 766, 728, 698, 665, 654, 612, 582, 558, 532, 496, 3,6-dihyro-2H-pyridin-1-yl]-propylamine to yield 3-{3-[4-(4-Chloro-phenyl)-434, 415, 403; Analysis calculated for $C_{23}H_{21}ClF_3N_3O_2 \cdot C_4H_4O_4 \cdot 4H_2O$; C, 49.74; H, 5.10; N, 6.44; Found: C, 49.62; H, 3.84; N, 6.43.

Example 32

Preparation of 8-Chloro-3-{3-[4-(3-chloro-phenyl)-3,6-dihydro-2H-pyridin-1-yl]propyl}-1H-quinazoline-2,4-dione The same general procedure was followed as in Example 7 with starting materials, 2-amino-3-chloro-benzoic acid, methyl ester and 3-[4-(3-Chloro-phenyl)-3,6-dihyro-2H-pyridin-1-yl]-propylamine to yield 8-Chloro-3-{3-[4-(3-chloro-phenyl)-3,6-dihydro-2H-pyridin-1-yl]-propyl}-1H-quinazoline-2,4-dione. The maleate salt of the compound has the following was found to have: M.p. 210–215° C.; $^1$H NMR DMSO-d$_6$ δ 11.07 (brd s, 1H), 7.92 (d, J=8 Hz, 1H), 7.83–7.77 (m, 1H), 7.56 (m, 1H), 7.47–7.33 (m, 3H), 7.21 (t, J=8 Hz, 1H), 6.31–6.23 (m, 1H), 5.99 (s, 2H), 4.03–3.95 (m, 2H), 3.82–3.57 (m, 2H), 3.26–3.13 (m, 2H), 2.77–2.61 (m, 2H), 2.09–1.96 (m, 2H)); IR (KBr) 3358, 3157, 3072, 2965, 2844, 2309, 1716, 1649, 1614, 1579, 1504, 1477, 1437, 1411, 1387, 1360, 1317, 1271, 1171, 1138, 1078, 1030, 944, 872, 815, 762, 738, 721, 676, 665, 649, 612, 583, 554, 534, 522, 494, 478, 457, 443, 429,415,403.

Example 33

Preparation of 5-Methyl-3-[3-(4-m-tolyl-3,6-dihydro-2H-pyridin-1-yl)-propyl]-1H-quinazoline-2, 4-dione The same general procedure was followed as in Example 7 with starting materials, 2-amino-6-methyl-benzoic acid, methyl ester and 3-[4-(m-tolyl)-3,6-dihyro2H-pyridin-1-yl]-propylamine to yield 5-Methyl-3-[3-(4-m-tolyl-3,6-dihydro-2H-pyridin-1-yl)-propyl]-1H-quinazoline-2,4-dione. The maleate salt of the compound has the following was found to have: Mp. 155–160° C.; $^1$H NMR CDCl$_3$ δ 9.43(brd s, 1H), 7.43 (t, J=8 Hz, 1H), 7.23–7.19 (m, 1H), 7.15–7.09 (m, 3H), 6.99–6.92 (m, 2H), 6.04 (s, 2H), 5.97–5.93 (m, 1H), 4.18–4.07 (m, 4H), 3.79–3.49 (m, 2H), 3.41–2.87 (m, 4H), 2.74 (s, 3H), 2.33(s,3H), 2.31–2.23 (m, 2H); IR (KBr) 3196, 3009, 2969, 2917, 2392, 1716, 1655, 1617, 1598, 1478, 1459, 1440, 1413, 1380, 1354, 1310, 1298, 1282, 1250, 1199, 1167, 1095, 968, 942, 880, 857, 840, 795, 777, 750, 697, 653, 617, 581, 531, 508, 478, 445, 4223, 410.

Example 34

Preparation of 5-Methyl-3-{3-[4-(3-trifluoromethyl-phenyl)-3,6-dihydro-2H-pyridin-1-yl]-propyl}-1H-quinazoline-2,4-dione The same general procedure was followed as in Example 7 with starting materials, 2-amino-6-methyl-benzoic acid, methyl ester and 3-[4-(3-trifluoromethyl-phenyl)-3,6-dihydro-2H-pyridin-1-yl-propylamine to yield 5-Methyl-3-{3-[4-(3-trifluoromethyl-phenyl)-3,6-dihydro-2H-pyridin-1-yl]-propyl}-1H-quinazoline-2,4-dione. The maleate salt of the compound has the following was found to have: Mp. 158–160° C.; $^1$H NMR CDCl$_3$ δ 9.51 (s, 1H), 7.58–7.40 (m, 5H), 6.96 (t, J=9 Hz, 2H), 6.07–6.03 (m, 1H), 6.02 (s, 2H), 4.19–4.06 (m, 4H), 3.39–3.27 (m, 2H), 2.74 (s, 3H), 2.34–2.22 (m, 2H), 2.03 (s, 1H), 1.24 (t, J=7 Hz, 1H); IR (KBr) 3356, 3220, 3156, 3070, 2964, 2921, 2376, 1716, 1648, 1614, 1578, 1504, 1478, 1436, 1411, 1386, 1360, 1317, 1271, 1215, 1169, 1138, 1069, 945, 874, 816, 778, 762, 725, 686, 665, 649, 584, 546, 494, 478, 442, 415, 404; Analysis calculated for C$_{24}$H$_{24}$F$_3$N$_3$O$_2$·C$_4$H$_4$O$_4$; C, 60.10; H, 5.04; N, 7.51; Found: C, 59.96; H, 5.13; N, 7.48.

Example 35

Preparation of 3-{3-[4-(3-Chloro-phenyl)-3,6-dihydro-2H-pyridin-1-yl]propyl}-5-methyl-1H-quinazoline-2,4-dione The same general procedure was followed as in Example 7 with starting materials, 2-amino-6-methyl-benzoic acid, methyl ester and 3-[4-(3-Chloro-phenyl)3,6-dihyro-2H-pyridin-1-yl]-propyyamine to yield 3-{3-[4-(3-Chloro-phenyl)-3,6-dihydro-2H-pyridin-1-yl]-propyl}-5-methyl-1H-quinazoline-2,4-dione. The maleate salt of the compound has the following was found to have: Mp. 180–183° C.; $^1$H NMR CDCl$_3$ δ 11.35 (s, 2H), 9.46 (brd s, 1H), 7.52–7.34 (m, 5H), 6.99 dd, J=8, 18 Hz, 2H), 6.26 (brd s, 1H), 5.99(s, 2H), 4.00–3.92(m, 4H), 3.84–3.50(m, 2H), 3.25–3.08(m, 2H), 2.75–2.67(m, 2H), 2.66(s, 3H), 2.05–1.95(m, 2H); IR (KBr) 3196, 3008, 2969, 2342, 1944, 1715, 1653, 1617, 1595, 1479, 1413, 1381, 1354, 1309, 1297, 1283, 1250, 1199, 1167, 1097, 996, 967, 942, 915, 881, 858, 837, 795, 775, 749, 732, 691, 650, 617, 583, 537, 509, 478, 443, 424, 405.

Example 36

Preparation of 8-Chloro-3-[3-(4-m-tolyl-3,6-dihydro-2H-pyridin-1-yl)propyl]-1H-quinazoline-2,4-dione The same general procedure was followed as in Example 7 with starting materials, 2-amino-3-chloro-benzoic acid, methyl ester and 3-[4-(m-tolyl)-3,6-dihyro2H-pyridin-1-yl]-propylamine to yield 8-Chloro-3-[3-(4-m-tolyl-3,6-dihydro-2H-pyridin-1-yl)-propyl]-1H-quinazoline-2,4-dione. The maleate salt of the compound has the following was found to have: Mp. 214–216° C.; $^1$H NMR DMSO-d$_6$ δ 11.11 (s, 1H), 7.98 (dd, J=1, 8 Hz, 1H), 7.85(dd, J=1, 8 Hz, 1H), 7.33–7.25 (m, 4 H), 7.19–7.13 (m, 1H), 6.18 (brd s, 1H), 6.04 (s, 2H), 4.04 (t, J=6 Hz, 2H), 3.89–3.56 (m, 2H), 3.40–3.15 (m, 4H), 2.80–2.69 (m, 2H), 2.34 (s, 3H), 2.15–2.02 (m, 2H); IR (KBr) 3356, 3220, 3156, 3070, 2964, 2921, 2376, 1716, 1648, 1614, 1578, 1504, 1476, 1436, 1411, 1386, 1360, 1317, 1271, 1215, 1169, 1138, 1069, 945, 874, 816, 778, 762, 725, 686, 665, 649, 584, 546, 494, 478, 442, 415, 404.

Example 37

Preparation of 5-Methyl-3-[3-(6-methyl-3',6'-dihydro-2'H-[2,4'bipyridinyl-1'-yl)-propyl]-1H-quinazoline-2,4-dione The same general procedure was followed as in Example 7 with starting materials, 2-amino-6-methyl-benzoic acid, methyl ester and 3-(6-methyl-3',6'-dihydro2'H-[2,4'bipyridinyl-1'-yl)-propylamine to yield 5-Methyl-3-[3-(6-methyl-3',6'-dihydro-2'H-[2,4'bipyridinyl-1'-yl)-propyl]-1H-quinazoline-2,4-dione. The maleate salt of the compound has the following was found to have: Mp. 200–203° C.; $^1$H NMR DMSO-d$_6$ δ 11.40 (s, 1H), 7.72 (t, J=8 Hz, 1H), 7.42 (d, J=10 Hz, 1H), 7.20 (d, J=8 Hz, 1H), 7.10–6.99 (m, 2H), 6.71–6.66 (m, 1H), 6.04 (s, 2H), 4.04–3.43 (m, 6H), 3.30–3.20 (m, 2H), 2.93–2.72 (m, 2H), 2.71 (s, 3H), 2.14–2.02 (m, 2H); IR (KBr) 3194, 3008, 2945, 2430, 1958, 1719, 1657, 1616, 1574, 1459, 1409, 1360, 1299, 1284, 1250, 1213, 1169, 1065, 995, 942, 900, 885, 873, 843, 811, 794, 752, 699, 692, 674, 649, 615, 583, 538, 508, 480, 468, 427; Analysis calculated for C$_{23}$H$_{26}$N$_4$O$_2$·C$_4$H$_4$O$_4$; C, 64.02; H, 5.97; N, 11.06. Found: C, 64.01; 11.05.

Example 38

Preparation of 4-Hydroxy-4-quinolin-2-yl-piperidine-1-carboxylic Acid Tert-butyl Ester A solution of 2-bromoquinoline (2.0 g, 9.61 mmol) in tetrahydrofuran (10 mL) was added dropwise to a mixture of n-butyllithium in hexane (4.2 mL of a 2.5 M solution) and tetrahydrofuran (10 mL) at −65° C. under N$_2$, and the mixture was stirred at this temperature for 1 hour. A solution of t-butyl-4-oxo-1-piperidine carboxylate (1.92 g, 9.61 mmol) in tetrahydrofuran (10 niL) was added dropwise over 3 minutes., after the addition, the reaction was slowly warmed to ambient temperature and stirred for 16 hours. The reaction was quenched with sat. ammonium chloride (15 mL); the resulting mixture was stirred at ambient temperature for 10 minutes. The organic layer was separated, washed with water (20 mL), brine (20 mL), dried over magnesium sulfate. Concentration yielded 4-hydroxy-4-quinolin-2-yl-piperidine-1-carboxylic acid tert-butyl ester (3.16 g, 98%) as a yellow oil which was used without further purification. $^1$H NMR CDCl$_3$ δ 8.20 (d, J=9 Hz, 1H), 8.08 (d, J=8 Hz, 1H), 7.83 (d, J=8 Hz, 1H), 7.73 (t, J=8 Hz, 1H), 7.55 (t, J=7 Hz, 1H), 7.42 (d, J=9 Hz, 1H), 5.94 (brd s, 1H), 4.23–4.00 (m, 2H), 3.70 (t, J=6 Hz, 1H), 3.40–3.22 (m, 2H), 2.42 (t, J=6 Hz, 1H), 2.13–1.98(m, 2H), 1.49 (s, 9H).

Example 39

Preparation of 4-Quinolin-2-yl-3,6-dihydro-2H-pyridine-1-carboxylic Acid Tert-butyl Ester 4-Hydroxy-4-quinolin-2-yl-piperidine-1-carboxylic acid tert-butyl ester (3.16 g, 9.61 mmol) and (methoxycarbonylsulfamoyl)triethylammonium hydroxide, inner salt (5.00 g, 20.98 mmol) in benzene (60 mL) under $N_2$ were refluxed for 3 hours. The solution was cooled to ambient temperature, diluted with water (50 mL) and the resulting mixture was stirred at ambient temperature for 10 minutes. The benzene layer was separated, washed with brine, dried over magnesium sulfate and concentrated onto silica gel; flash chromatography using an ethyl acetate/hexanes gradient gave 4-quinolin-2-yl-3,6-dihydro-2H-pyridine-1-carboxylic acid tert-butyl ester (1.65 g, 55%) as a yellow oil. $^1$H NMR CDCl$_3$ δ 8.09 (d, J=9 Hz, 1H), 8.03 (d, J=8 Hz, 1H), 7.76 (d, J=8 Hz, 1H), 7.70–7.63 (m, 1H), 7.56 (d, J=9 Hz, 1H), 7.51–7.44 (m, 1H), 6.69–6.63 (m, 1H), 4.21–4.14 (m, 2H), 3.68 (t, J=6 Hz, 1H), 2.87–2.80 (m, 2H), 1.48 (s, 9H).

Example 40

Preparation of 2-(1,2,3,6-Tetrahydro-pyridin-4-yl)-quinoline

A solution of 4-quinolin-2-yl-3,6-dihydro-2H-pyridine-1-carboxylic acid tert-butyl ester (0.072 g, 0.23 mmol) in methylene chloride (5 mL) was added dropwise to a solution of trifluoroacetic acid at 0° C. under $N_2$. After stirring for 45 minutes. at 0° C., the reaction was concentrated to a yellow oil which was slurried in 5% sodium carbonate (5 mL) and stirred for 30 minutes. at ambient temperature. The mixture was concentrated to a yellow solid; the solid was triturated with chloroform (20 mL) which was dried over sodium sulfate. Concentration yielded 2-(1,2,3,6-tetrahydro-pyridin-4-yl)-quinoline (46 mg, 96%) as a yellow oil which was used without further purification. $^1$H NMR CDCl$_3$ δ 8.06 (d, J=9 Hz, 1H), 8.03 (d, J=9 Hz, 1H), 7.75 (d, J=8 Hz, 1H), 7.68–7.63 (m, 1H), 7.55 (d, J=9 Hz, 1H), 7.46 (t, J=8 Hz, 1H), 6.75–6.40 (m, 1H), 3.70–3.65 (m, 2H), 3.42–3.29 (m, 1H), 3.20 (t, J=6 Hz, 2H), 2.85–2.78 (m, 2H).

Example 41

Preparation of 2-[3-(2-[1,3Dioxolan-2-yl-ethyl)-ureido]-benzoic Acid Methyl Ester Methylanthranilate (1.18 g, 7.79 mmol) and triethylamine (2.5 mL, 17.7 mmol) in methylene chloride (10 mL) were cooled in an ice bath. Triphosgene (0.69 g, 2.34 mmol) in methylene chloride (10 ml) was added dropwise over 10 minutes. and the resulting mixture was stirred for 1 hour at 0° C. to form the isocyanate intermediate. 2-(2-Aminoethyl)-1,3-dioxolane(2.00 g, 17.1 mmol) in methylene chloride (10 ml) was added dropwise at 0° C. over 10 minutes., then the mixture was warmed to ambient temperature and stirred for 15 hours. Concentration yielded a yellow solid which was taken up in ethyl acetate and sat. sodium bicarbonate solution; the layers were separated. The organic layer was washed with brine, dried over magnesium sulfate. Concentration yielded 2-[3-(2-[1,3dioxolan-2-yl-ethyl)-ureido]-benzoic acid methyl ester (1.26 g, 60%) as a white solid. $^1$H NMR CDCl$_3$ δ 10.26 (brd s, 1H), 8.51–8.44 (m, 1H), 7.95 (dd, J=2, 8 Hz, 1H), 7.49–7.44 (m, 1H), 6.95–6.91 (m, 1H), 5.35–5.10 (brd s, 1H), 4.95 (t, J=4 Hz, 1H), 4.01–3.98 (m, 2H), 3.88 (S, 3H), 3.87–3.82 (m, 2H), 3.44 (t, J=6 Hz, 2H), 1.96–1.92 (m, 2H).

Example 42

Preparation of 3-(2-[1,3Dioxolan-2-yl-ethyl)-1H-quinazoline-2,4-dione

A white mixture of 2-[3-(2-[1,3dioxolan-2-yl-ethyl)-ureido]-benzoic acid methyl ester (0.50 g, 1.70 mmol) and 1N sodium hydroxide (2.0 mL) in ethanol (10 mL) was warmed until all the solids had gone into solution. The resulting colorless solution was cooled to ambient temperature and stirred for 30 minutes. Concentration yielded a colorless foam which was dissolved in water (15 mL); after 15 minutes, a white crystalline solid formed. The white crystalline solid was collected and dried to yield 3-(2-[1,3dioxolan-2-yl-ethyl)-1H-quinazoline-2,4-dione (0.19 g, 43%). $^1$H NMR CDCl$_3$ δ 7.92 (dd, J=1, 8 Hz, 1H), 7.67–7.61 (m, 1H), 7.22–7.15 (m, 2H), 4.88 (t, J=4 Hz, 1H), 4.00 (t, J=7 Hz, 2H), 3.89–3.71 (m, 4H), 1.93–1.86 (m, 2H).

Example 43

Preparation of 3-[2,4-Dioxo-1,4-dihydro-2H-quinazolin-3-yl]propionaldehyde

A solution of 3-(2-[1,3dioxolan-2-yl-ethyl)-1H-quinazoline-2,4-dione (0.11 g, 0.43 mmol), 10% sulfuric acid (10 mL) and Acetone (10 mL) was stirred at ambient temperature for 24 hours. Concentration yielded 3-[2,4-dioxo-1,4-dihydro-2H-quinazolin-3-yl]propionaldehyde (0.09 g, 95%) as an off-white solid. $^1$H NMR CDCl$_3$ δ 9.85 (s, 1H), 8.10–8.06 (m,1H), 7.63–7.57 (m, 1H), 7.24–7.19 (m, 1H), 7.13–7.07 (m, 1H), 4.44–4.40 (m, 2H), 2.85 (dt, 2H, $J_{1,2}$=2 Hz, $J_{1,3}$=7 Hz).

Example 44

Preparation of 3-[3-(4-Quinolin-2-yl-3,6-dihydro-2H-pyridin-1-yl)-propyl]-1H-quinazoline-2,4-dione 3-[2,4-Dioxo-1,4-dihydro-2H-quinazolin-3-yl] propionaldehyde (0.042 g, 0.19 mmol), 2-(1,2,3,6-tetrahydro-pyridin-4-yl)-quinoline (0.049 g, 0.23 mmol), sodium triacetoxyborohydride (0.204 g, 0.96 mmol) and dichloroethane (10 mL) were combined at ambient temperature, and stirred for 72 hours. The reaction was diluted with 1 N HCl solution (10 mL), and stirred for 30 min. The organic phase was collected, washed with brine (20 mL), dried over magnesium sulfate and concentrated onto silica gel; flash chromatography using an ethyl acetate/hexanes gradient gave 3-[3-(4-quinolin-2-yl-3,6-dihydro-1-yl)-propyl]-1H-quinazoline-2,4-dione as a white solid. maleate salt: Mp. 195–200° C.(decomposed); $^1$H NMR CDCl$_3$ δ 11.54 (s,1H), 11.45–11.42 (m, 2H), 8.44–8.37 (m, 1H), 8.02–7.93 (m, 4H), 7.29–7.17 (m, 4H), 6.95–6.86 (m, 1H), 6.06 (s, 2H), 5.65–5.57 (m, 1H), 4.67–4.52 (m, 4H), 4.09–3.94 (m, 4H), 3.83–3.72 (m, 2H), 3.03–2.70 (m, 2H), 2.21–2.05 (m, 2H); IR (KBr) 3208, 3061, 2938, 2576, 1953, 1716, 1656, 1620, 1492, 1454, 1410, 1356, 1276, 1238, 1209, 1171, 1122, 1108, 1054, 1018, 961, 869, 811, 784, 757, 693, 682, 657, 615, 561, 529,465, 420,408.

Example 45

Preparation of 3-Chloro-2-[3-(3-chloro-propyl)-ureido]-benzoic Acid

A 250 mL round bottom flask is charged with 2-amino-3-chlorobenzoic acid (5.00 g, 29.1 mmol) and 100 mL of 5% aqueous KHCO$_3$. The slurry is cooled to 0° C., and 3-chloropropylisocyanate (6.0 mL, 58 mmol) is added. The mixture is then allowed to warm to room temperature over 16 hours. HPLC analysis shows some starting material remaining, so the solution is recooled to 0° C. and an additional portion of the isocyanate (3.0 mL, 29 mmol) is added. After 2 h, the solution is acidified with 1 N HCl (ca. 40 mL), and the resulting yellow solid is filtered, rinsing with 1 N HCl. The resulting solid (35.5 g) is recrystallized from 80 mL of hot ethanol, to provide the product as a white solid: 4.22 g, 14.5 mmol, 50% yield. M.p. 124.4–124.8° C. $^1$H NMR (CD$_3$OD): 7.84 (d, J=8,1H), 7.64 (d, J=8,1H), 7.24 (t, J=8,1H), 3.68 (t, J=7, 2H), 3.37 (t, J=6, 2H), 2.01 (m, 2H). MS (CI): 289 (M-H, 100), 196 (M-ClCH$_2$CH$_2$CH$_2$NH, 25).

Example 46

Preparation of 8-Chloro-3,4-dihydro-2H-1-oxa-4a,9-diaza-anthracen-10-one

A 250 mL round bottom flask is charged with 3-chloro-2-[3-(3-chloro-propyl)-ureido]-benzoic acid (3.40 g, 11.7 mmol) and 50 mL of 10% aqueous KHCO$_3$, and warmed to reflux for 1 hour. 50 mL of H$_2$O is added and the solution is allowed to cool to room temperature, then to 0° C. The resulting yellow solid is collected by filtration to provide 2.32 g of crude product, which is recrystallized from CH$_2$Cl$_2$-isopropyl ether to provide the product as a white solid: 1.10 g (4.6 mmol, 40% yield). M.p. 206.7–207.9° C. $^1$H NMR (CDCl$_3$): 8.09 (d, J 8, 1H), 7.77 (d, J=8, 1H), 7.24 (t, J=8, 1H), 4.54 (t, J=5, 2H), 4.14 (t, J=6, 2H), 2.32 (m, 2H). MS (CI): 237 (M+H, 100).

Example 47

Preparation of 8-Chloro-3,4-dihydro-2H-1-oxa-4a,9-diaza-anthracen-10-one

A 250 mL round bottom flask is charged with 2-amino-3-chlorobenzoic acid (5.00 g, 29.1 mmol) and 40 mL of 10% aqueous KHCO$_3$. The slurry is cooled to 0° C., and 3-chloropropylisocyanate (5.25 mL, 51.2 mmol) is added. The reaction mixture is allowed to warm to room temperature over 3 h, warmed to reflux for 2 h, then stirred at room temperature for 16 h. It is then diluted with 40 mL H$_2$O and cooled to 0° C. The product is collected by filtration to provide 5.68 g of a yellow solid. This material is purified by recrystallization: it is dissolved in a minimal volume of warm CH$_2$Cl$_2$ (ca. 10 mL), cooled to 0° C., and IPE (ca. 20 mL) added to the point of cloudiness; crystallization is allowed to proceed at that temperature for 1 h. The resulting yellow solid is collected and dried to provide 3.87 g (16.3 mmol, 56% yield) of light yellow solid.

What is claimed is:

1. A compound of the formula (I):

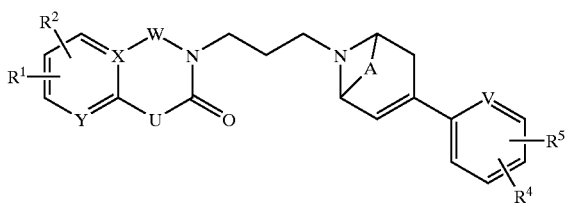

(I)

or a pharmaceutically acceptable salt thereof, wherein:

A is (CH$_2$)$_n$ where n is equal to 0, 1 or 2, with the proviso that when n is 0 there is no bridging group A;

U is NH or NR$^3$,

R$^1$ and R$^2$ are selected independently from H, (C$_1$–C$_6$) alkyl, Cl, F, CN, nitro, CF$_3$, —NHC(O)R$^6$ and —OR$^7$;

R$^3$ is selected from the group consisting of (C$_1$–C$_6$)$_m$alkyl, C(=O)—(C$_1$–C$_6$)alkyl, where m=1 or 2;

R$^4$ and R$^5$ are selected from H, (C$_1$–C$_6$)alkyl, Cl, F, —CF$_3$, —CN, —NHC(=O)R$^6$, —OR$^7$, a 5- to 7-membered aryl or heteroaryl ring, where m, R$^6$ and R$^7$ are as defined above; and R$^6$ and R$^7$ are selected independently from H, (C$_1$–C$_6$) alkyl or a 5- to 7-membered aryl or heteroaryl ring;

V is CH, CR$^3$, or N;

W is CH$_2$ or C(O);

X is C;

Y is CH, CR$^1$ or CR$^2$ where R$^1$ and R$^2$ are as defined above.

2. A compound according to claim 1 wherein A is (CH$_2$)$_n$ where n is equal to 1 or 2; and pharmaceutically acceptable salts thereof.

3. A compound according to claim 1 wherein n is equal to zero and there is no bridging group A; W is C(=O); X is C; Y is CH; V is CH or N; and pharmaceutically acceptable salts thereof.

4. A compound according to claim 1 wherein n is equal to zero; W is C(=O); X is C; Y is CH; V is CH or N; U is NH, and R$^1$, R$^2$, R$^4$, R$^5$ are independently chosen from the group consisting of hydrogen, halo, —CF$_3$, nitro, (C$_1$–C$_6$)alkyl, hydroxy or methoxy; and pharmaceutically acceptable salts thereof.

5. A compound according to claim 1 wherein n is equal to zero and there is no bridging group A; W is C(=O); X is C; Y is CH; V is CH; U is NH, and R$^1$, R$^2$, R$^4$, R$^5$ are independently chosen from the group consisting of hydrogen, halo, —CF$_3$, nitro, (C$_1$–C$_6$)alkly, hydroxy or methoxy; and pharmaceutically acceptable salts thereof.

6. A compound according to claim 1 selected from the group consisting of:

3-{3-[4-(4-Chloro-phenyl)-3,6-dihydro-2H-pyridinyl-1-yl]-propyl}-6-methyl-1H-quinazoline-2,4-dione;

3-{3-[4-(4-Chloro-phenyl)-3,6-dihydro-2H-pyridinyl-1-yl]-propyl}-8-methoxy-1H-quinazoline-2,4-dione;

3-{3-[4-(4-Chloro-phenyl)-3,6-dihydro-2H-pyridinyl-1-yl]-propyl}-8-chloro-1H-quinazoline-2,4-dione; and 5-Methyl-3-[3-(4-m-tolyl-3,6-dihydro-2H-pyridin-1-yl)-propyl]-1H-quinazoline-2,4-dione;

3-{3-[4-(4-Chloro-phenyl)-3,6-dihydro-2H-pyridin-1-yl]-propyl}-5-fluoro-1H-quinazoline-2,4-dione;

3-{3-[4-(4-Chloro-phenyl)-3,6-dihydro-2H-pyridin-1-yl]-propyl}-6-fluoro-1H-quinazoline-2,4-dione;

3-{3-[4-(4-Chloro-phenyl)-3,6-dihydro-2H-pyridin-1-yl]-propyl}-7-fluoro-1H-quinazoline-2,4-dione;

3-{3-[4-(4-Chloro-phenyl)-3,6-dihydro-2H-pyridin-1-yl]-propyl}-6,7-difluoro-1H-quinazoline-2,4-dione;

and pharmaceutically acceptable salts thereof.

7. A method for preparing a compound of formula (I):

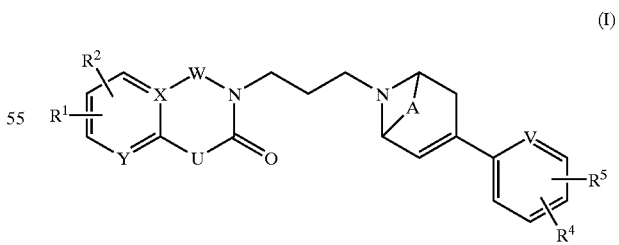

(I)

wherein:

A is (CH$_2$)$_n$ where n is equal to 0, 1 or 2, with the proviso that when n is 0 there is no bridging group A;

U is NH, or NR$^3$,

R$^1$ and R$^2$ are selected independently from H, (C$_1$–C$_6$) alkyl, Cl, F, CN, nitro, CF$_3$, —NHC(O)R$^6$ and —OR$^7$;

$R^3$ is selected from the group consisting of $(C_1-C_6)_m$alkyl, $C(=O)-(C_1-C_6)$alkyl, where m=1 or 2;

$R^4$ and $R^5$ are selected from H, $(C_1-C_6)$alkyl, Cl, F, $-CF_3$, $-CN$, $-NHC(=O)R^6$, $-OR^7$, a 5- to 7-membered aryl or heteroaryl ring, where m, $R^6$ and $R^7$ are as defined above;

$R^6$ and $R^7$ are selected independently from H, $(C_1-C_6)$ alkyl or a 5- to 7-membered aryl or heteroaryl ring;

V is CH, $CR^3$, or N;

W is $CH_2$ or C(O);

X is C;

Y is CH, $CR^1$ or $CR^2$;

comprising the step of allowing a compound of formula (AII):

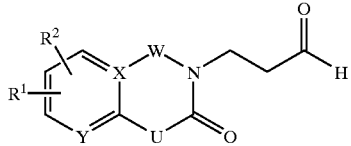

wherein U, W, X, Y, $R^1$ and $R^2$ are as defined above, to react with a compound of formula (BI):

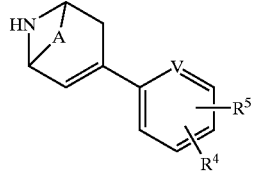

wherein A, V, $R^4$ and $R^5$ are as defined above in an inert solvent in the presence of a triacetoxy borohydride salt at a temperature from 0° C. to 150° C. for a period up to 72 hours.

8. The method according to claim 7 wherein U is NH; U is N; V is CH or N; W is carbonyl; X is C; n is 0 and there is no bridging group A; and Y is C.

9. The method according to claim 7 wherein n is 1 or 2.

10. A method of inhibiting serotonin reuptake or 5-$HT_{2A}$ serotonin receptor binding in the central nervous system of a mammal comprising the administration to the mammal a serotonin receptor binding-inhibiting effective amount or a serotonin reuptake-inhibiting effective amount of a compound of claim 1.

11. A method of treating a mammal for a disease, condition or disorder of the central nervous system, said method comprising the administration to the mammal a therapeutically effective amount of a compound of claim 1.

12. The method according to claim 11 wherein the disease, condition or disorder of the central nervous system is selected from the group consisting of aggression disorder; anxiety disorder selected from the group consisting of panic attack, agoraphobia, panic disorder with or without agoraphobia, agoraphobia without history of panic disorder, obsessive-compulsive disorder, post-traumatic stress disorder and acute stress disorder; cognitive disorder selected from the group consisting of amnestic disorders, deliriums, dementias; emesis; food behavior disorder selected from anorexia nervosa and bulimia, headache disorder selected from the group consisting of migraine, cluster and vascular headaches; learning disorder selected from attention deficit disorder and attention deficit/hyperactivity disorder; obesity; psychotic condition selected from the group consisting of schizophrenia, schizophreniform disorder, schizoaffective disorder, delusional disorder, brief psychotic disorder, psychotic disorder due to a general medical condition and psychotic disorders not otherwise specified; sleep disorder selected from the group consisting of primary sleep disorders, sleep disorders related to another mental disorder, sleep disorders due to a general medical condition and sleep disorders not otherwise specified; sexual behavior disorder; substance-abuse disorder selected from the group consisting of alcohol-related disorders, amphetamine-related disorders, caffeine-related disorders, cannabis-related disorders, cocaine-related disorders, hallucinogen-related disorders, inhalant-related disorders, nicotine-related disorders, opioid-related disorders, phencyclidine-related disorders, sedative-related disorders, hypnotic-related disorders, anxiolytic-related disorders and polysubstance-related disorder and vision disorders.

13. A pharmaceutical composition comprising a therapeutically effective amount of the compound of claim 1 and a pharmaceutically acceptable carrier.

14. A pharmaceutical composition comprising a pharmaceutically acceptable carrier and a serotonin reuptake-inhibiting effective amount or a serotonin binding-inhibiting effective amount of the compound of claim 1.

* * * * *